United States Patent [19]

Tanouchi et al.

[11] 4,271,170

[45] Jun. 2, 1981

[54] PYRIDINE DERIVATIVES

[75] Inventors: Tadao Tanouchi; Masanori Kawamura; Masaki Hayashi, all of Osaka, Japan

[73] Assignees: Ono Pharmaceutical Co., Ltd.,, Osaka; Kissei Pharmaceutical Co., Ltd., Magano, both of Japan

[21] Appl. No.: 105,672

[22] Filed: Dec. 20, 1979

[30] Foreign Application Priority Data

Dec. 28, 1978 [JP] Japan ............................. 53/161966
Aug. 7, 1979 [JP] Japan ............................. 54/100377

[51] Int. Cl.$^3$ .................. A61K 31/44; C07D 213/55; C07D 409/06
[52] U.S. Cl. .................................. 424/263; 546/284; 546/333; 546/335; 546/340; 546/342; 546/343; 546/344
[58] Field of Search .............. 424/263; 546/284, 333, 546/335, 340, 342

[56] References Cited

FOREIGN PATENT DOCUMENTS 1119334 7/1968 United Kingdom .
1446574 8/1976 United Kingdom .
1448366 9/1976 United Kingdom .
1471276 4/1977 United Kingdom .

OTHER PUBLICATIONS

Chem. Abstr. 84, 42694n (1976).
Chem. Abst. 78, 136094b (1973).
Sinsheimer et al., J. Med. Chem., 1976, vol. 19(5), pp. 647-650.
Fields et al., J. Organic Chem., vol. 35, No. 6, (1970), pp. 1870-1875.

*Primary Examiner*—Henry R. Jiles
*Assistant Examiner*—Bernard Dentz
*Attorney, Agent, or Firm*—Sughrue, Rothwell, Mion, Zinn and Macpeak

[57] ABSTRACT

The pyridine derivatives of the general formula:

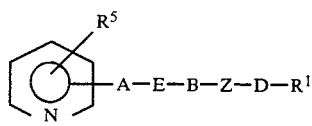

[wherein A represents an alkylene group containing from 1 to 5 carbon atoms unsubstituted or substituted by a hydroxy group, B represents a single bond, or an oxygen or sulphur atom, or an alkylene group containing from 1 to 5 carbon atoms, D represents a single bond, or an alkylene group containing from 1 to 5 carbon atoms, R represents a grouping of the formula:

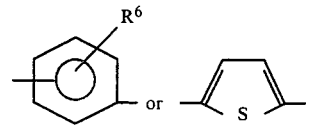

(in which $R^6$ represents a hydrogen atom, or an alkyl group containing from 1 to 4 carbon atoms), Z represents a single bond, or an ethynylene group, or a grouping of the formula:

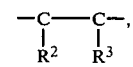

in which $R^2$ represents a hydrogen atom, or an alkyl group containing from 1 to 4 carbon atoms, $R^3$ represents a hydrogen, bromine or chlorine atom, or an alkyl group containing from 1 to 4 carbom atoms; the symbol ═════ represents a single or double bond, the carbon atom attached to $R^2$ binds to B, and the carbon atom attached to $R^3$ binds to D, $R^1$ represents a hydroxy group, or a grouping of the formula: -COOR$^4$ or -COSR$^4$, in which $R^4$ represents a hydrogen atom, or an alkyl group containing from 1 to 12 carbon atoms, or an aralkyl group containing from 7 to 33 carbon atoms, or a cycloalkyl group containing from 4 to 7 carbon atoms unsubstituted or substituted by at least one alkyl group containing from 1 to 4 carbon atoms, or a phenyl unsubstituted or substituted by at least one halogen atom, trifluoromethyl group, alkyl or alkoxy or alkylthio group containing from 1 to 4 carbon atoms, nitro or phenyl group, $R^5$ represents a hydrogen atom, or an alkyl group containing from 1 to 4 carbon atoms, with the proviso that, when B represents an oxygen or sulphur atom, Z represents a single bond and D represents an alkylene group containing from 1 to 5 carbon atoms], and non-toxic acid addition salts thereof and, when $R^1$ represents a carboxy or thiocarboxy group, non-toxic salts thereof, possess a strong inhibitory activity on thromboxane synthetase from rabbit platelet microsomes, and are useful as therapeutically active agents in the prevention or treatment of inflammation, hypertension, thrombus, cerebral apoplexy, asthma, myocardial infarction, cardiostenosis, cerebral infarction and acute cardiac death.

76 Claims, No Drawings

PYRIDINE DERIVATIVES

This invention relates to pyridine derivatives, to processes for their preparation and to pharmaceutical compositions containing them.

Up to now, of the compounds having a pyridine skeleton, it has been reported that 2-isopropyl-3-nicotinylindole(L-8027) possesses an inhibitory activity on thromboxane synthetase [FEBS. Lett., 82, 107(1977)]. Also, it has been known that (i) sodium p-benzyl-4-[1-oxo-2-(4-chlorobenzyl)-3-phenylpropyl]phenylphosphonate(N-0164), (ii) prostaglandins, e.g. 9,11-epoxymethanoprostanoic acid, 9,11-epoxymethano-15-hydroxyprosta-5,13-dienoic acid and 9,11-azo-15-hydroxyprosta-5,13-dienoic acid, (iii) imidazoles, e.g. imidazole and 1-methylimidazole, (iv) nordihydroguaiaretic acid, and (v) 12L-hydroperoxy-5,8,10,14-eicosatetraenoic acid(HPETE) possess an inhibitory activity on thromboxane synthetase [Annual Review of Biochemistry, 47, 1002-4(1978)]. However, their inhibitory activity on thromboxane synthetase is very weak, the above-mentioned compounds are unsatisfactory as practically effective medicines.

Widespread investigations have been carried out in order to discover inter alia new pyridine derivatives possessing a much stronger and more specific inhibitory effect on thromboxane synthetase. As a result of extensive research and experimentation, it has now been discovered that by introducing a grouping —A—E—B—Z—D—$R^1$ (in which the various symbols are as hereafter defined) into a pyridine ring, the pharmacological properties of the aforementioned compounds are enhanced.

Accordingly, the present invention resides in one aspect in pyridine derivatives of the general formula:

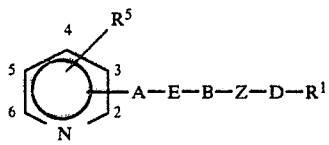

I

[wherein A represents an alkylene group containing from 1 to 5 carbon atoms unsubstituted or substituted by a hydroxy group, B represents a single bond, or an oxygen or sulphur atom, or an alkylene group containing from 1 to 5 carbon atoms, D represents a single bond, or an alkylene group containing from 1 to 5 carbon atoms, E represents a grouping of the formula:

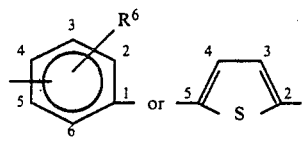

(in which $R^6$ represents a hydrogen atom, or an alkyl group containing from 1 to 4 carbon atoms), Z represents a single bond, or an ethynylene group, i.e. —C≡C—, or a grouping of the formula:

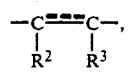

(in which $R^2$ represents a hydrogen atom, or an alkyl group containing from 1 to 4 carbon atoms, $R^3$ represents a hydrogen, bromine or chlorine atom, or an alkyl group containing from 1 to 4 carbon atoms, the symbol ≡≡≡ represents a single or double bond, the carbon atom attached to $R^2$ binds to B, and the carbon atom attached to $R^3$ binds to D), $R^1$ represents a hydroxy group, or a grouping of the formula: —$COOR^4$ or —$COSR^4$ (in which $R^4$ represents a hydrogen atom, or an alkyl group containing from 1 to 12 carbon atoms, or an aralkyl group containing from 7 to 13 carbon atoms, or a cycloalkyl group containing from 4 to 7 carbon atoms unsubstituted or substituted by at least one alkyl group containing from 1 to 4 carbon atoms, or a phenyl group unsubstituted or substituted by at least one halogen atom, trifluoromethyl group, alkyl or alkoxy or alkylthio group containing from 1 to 4 carbon atoms, nitro or phenyl group), $R^5$ represents a hydrogen atom, or an alkyl group containing from 1 to 4 carbon atoms, with the proviso that, when B represents an oxygen or sulphur atom, Z represents a single bond and D represents an alkylene group containing from 1 to 5 carbon atoms], and non-toxic acid addition salts thereof and, when $R^1$ represents a carboxy or thiocarboxy group, non-toxic salts thereof.

The invention further resides in processes for the preparation of the pyridine derivatives described in the preceding paragraph and to pharmaceutical compositions containing the derivatives.

Preferably the pyridine is substituted by A at the 3-position and substituted by $R^5$ at the 4-position, or vice versa. Preferably the benzene is substituted by A at the 4-position (i.e. p-position) and substituted by $R^6$ at the 3-position (i.e. m-position), or vice versa.

It is to be understood that alkyl and alkylene groups and alkyl and alkylene moieties of groups referred to in this specification and the accompanying claims may be straight- or branched-chain.

Examples of the alkylene group containing from 1 to 5 carbon atoms represented by A, B and D are methylene, ethylene, trimethylene, tetramethylene, pentamethylene, and their isomers.

Examples of the alkyl group containing from 1 to 4 carbon atoms represented by $R^2$, $R^3$, $R^5$ and $R^6$ are methyl, ethyl, propyl, isopropyl, butyl, isobutyl, sec-butyl and tert-butyl.

Examples of the alkyl group containing from 1 to 12 carbon atoms represented by $R^4$ are methyl, ethyl, propyl, butyl, pentyl, hexyl, heptyl, octyl, nonyl, decyl, undecyl, dodecyl, and their isomers.

Examples of the aralkyl group containing from 7 to 13 carbon atoms represented by $R^4$ are benzyl, 1-phenylethyl, 2-phenylethyl, 3-phenylbutyl, 4-phenylbutyl, 1-(2-naphthyl)ethyl, 2-(1-naphthyl)ethyl and biphenylmethyl.

Examples of the cycloalkyl group containing from 4 to 7 carbon atoms unsubstituted or substituted by at least one alkyl group containing from 1 to 4 carbon atoms represented by $R^4$ are cyclobutyl, 1-propylcyclobutyl, 1-butylcyclobutyl, 2-methylcyclobutyl, 2-propylcyclobutyl, 3-ethylcyclobutyl, 3-propylcyclobutyl, 2,3,4-triethylcyclobutyl, cyclopentyl, 3-ethylcyclopentyl, 3-propylcyclopentyl, 3-butylcyclopentyl, 3-tert-butylcyclopentyl, 2,2-dimethylcyclopentyl, (1-methyl-3-propyl)cyclopentyl, (2-methyl-3-propyl)cyclopentyl, (2-methyl-4-propyl)cyclopentyl, cyclohexyl, 3-ethylcyclohexyl, 3-isopropylcyclohexyl, 4-methylcyclohexyl, 4-ethylcyclohexyl, 4-propylcyclohexyl, 4-tert-butylcyclohexyl, 2,2-dimethylcyclohexyl, 2,6-dimethylcyclohexyl, (2,6-dimethyl-4-propyl)cyclohexyl and cycloheptyl.

Examples of the phenyl group unsubstituted or substituted by at least one halogen atom, trifluoromethyl group, alkyl or alkoxy or alkylthio group containing from 1 to 4 carbon atoms, or nitro or phenyl group represented by $R^4$ are phenyl, 2-, 3- or 4-chlorophenyl, 2,4-dichlorophenyl, 2,4,6-trichlorophenyl, 2-, 3- or 4-tolyl, 2-, 3- or 4-ethylphenyl, 2-, 3- or 4-isopropylphenyl, 2-, 3- or 4-tert-butylphenyl, 4-sec-butylphenyl, 2,4-dimethylphenyl, 2,5-dimethylphenyl, 2,6-dimethylphenyl, 2,6-diethylphenyl, (2-isopropyl-5-methyl)phenyl, 2,6-diisopropylphenyl, (2-tert-butyl-6-methyl)phenyl, (2-tert-butyl-4-methyl)phenyl, 2,4-di-tert-butylphenyl, 2,6-di-tert-butylphenyl, 3,5-di-tert-butylphenyl, 2,4,6-trimethylphenyl, (2-tert-butyl-4,6-dimethyl)phenyl, (2,6-di-tert-butyl-4-methyl)phenyl, 2,4,6-tri-tert-butylphenyl, 3-trifluoromethylphenyl, 4-biphenyl, 2-, 3- or 4-methoxyphenyl, 2-, 3- or 4-ethoxyphenyl, 2-, 3- or 4-methylthiophenyl, 2-, 3- or 4-ethylthiophenyl, and 2-, 3- or 4-nitrophenyl.

Preferably A is an alkylene group containing 1 or 2 carbon atoms unsubstituted or substituted by a hydroxy group, preferably B is a single bond, or an oxygen or sulphur atom, preferably Z is a single bond or the group

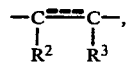

preferably $R^1$ is a grouping of the formula: —COOR$^4$ or —COSR$^4$, and preferably $R^4$ is a hydrogen atom, or an alkyl group containing from 1 to 10 carbon atoms, or an aralkyl group containing from 7 to 13 carbon atoms, or a phenyl group unsubstituted or substituted by at least one alkyl group containing from 1 to 4 carbon atoms, or trifluoromethyl group, more preferably $R^4$ is a hydrogen atom, or an alkyl group containing from 1 to 4 carbon atoms, or a decyl, benzyl, biphenylmethyl, 3-trifluoromethylphenyl, 3,5-di-tert-butylphenyl, 2-methylphenyl or phenyl group.

According to a feature of the present invention, the pyridine derivatives of general formula I, wherein B is other than oxygen and sulphur atoms, Z represents a grouping of the formula:

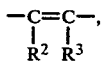

$R^1$ represents a grouping of the formula: —COOR$^4$, in which $R^4$ represents a hydrogen atom, or an alkyl group containing from 1 to 12 carbon atoms, and the other symbols are as hereinbefore defined, i.e. compounds of the general formula:

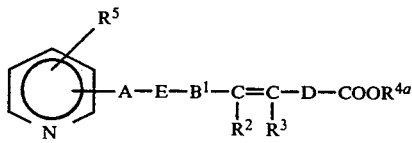

(wherein $B^1$ represents a single bond, or an alkylene group containing from 1 to 5 carbon atoms, $R^{4a}$ represents a hydrogen atom, or an alkyl group containing from 1 to 12 carbon atoms, and the other symbols are as hereinbefore defined) are prepared by the Wittig reaction of compounds of the general formula:

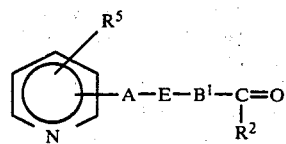

(wherein the various symbols are as hereinbefore defined) with, when D is a single bond, (1) a sodium derivative of dialkyl phosphonates of the general formula:

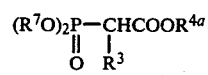

(wherein $R^7$ represents an alkyl group containing from 1 to 4 carbon atoms, preferably methyl or ethyl, and the other symbols are as hereinbefore defined), the sodium derivatives may be prepared from dialkyl phosphonates of general formula III and sodium hydride, or (2) a phosphorane compound of the general formula:

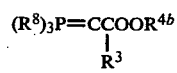

(wherein $R^{4b}$ represents an alkyl group containing from 1 to 12 carbon atoms, $R^8$ represents a phenyl group unsubstituted or substituted by at least one alkyl group containing from 1 to 4 carbon atoms, preferably phenyl, or an alkyl group containing from 1 to 6 carbon atoms, preferably butyl, or a cyclohexyl group, and $R^3$ is as hereinbefore defined) or, when D is an alkylene group, (3) an ylide of phosphonium compounds of the general formula:

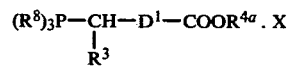

(wherein $D^1$ represents an alkylene group containing from 1 to 5 carbon atoms, X represents a halogen atom, and the other symbols are as hereinbefore defined).

The Witig reaction is described in 'Organic Reactions', Volume 14, Chapter 3(1965), John Wiley & Sons, Inc.(USA), preferably the Wittig reaction may be effected in an inert organic solvent, e.g. an ether such as diethyl ether, tetrahydrofuran, dioxene or 1,2-dimethoxyethane, a hydrocarbon such as benzene, toluene, xylene or hexane, a dialkyl sulphoxide such as dimethyl sulphoxide (hereinafter referred to as DMSO), a dialkylformamide such as N,N-dimethylformamide, a halogenated hydrocarbon such as methylene chloride or chloroform, or an alkanol containing from 1 to 4 carbon atoms such as methanol or ethanol, or a mixture of two or more of them, at a temperature of −78° C. to the reflux temperature of the reaction mixture.

The product, thus obtained, may be purified by conventional means, for example by thin layer, column or high-speed liquid chromatography on silica gel to give the desired E- or Z-compound of formula IA.

The ylide of compounds of general formula V may be prepared by reaction of phosphonium compounds of general formula V with an adequate base, e.g. butyllithium, lithium diisopropylamide, dimsyl sodium, sodium methoxide, potassium tert-butoxide or triethylamine.

Dialkyl phosphonate of general formula III, phosphorane compounds of general formula IV and phosphonium compounds of general formula V are well known, or may easily be prepared by methods known per se. By the term 'methods known per se' as used in this specification is meant methods heretofore used or described in the chemical literature.

The pyridine derivatives of general formula I, wherein B is other than oxygen and sulphur atoms, Z represents a grouping of the formula:

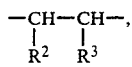

$R^1$ represents a grouping of the formula: —COOR$^4$, in which $R^4$ represents a hydrogen atom, or an alkyl group containing from 1 to 12 carbon atoms, and the other symbols are as hereinbefore defined, i.e. compounds of the general formula:

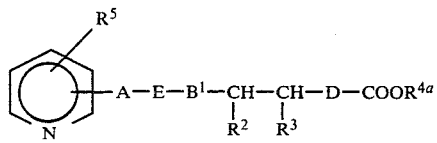

IB (wherein the various symbols are as hereinbefore defined) are prepared by hydrogenation of compounds of general formula IA by methods known per se.

The suitable hydrogenation may be effected under an atmosphere of hydrogen in the presence of an adequate hydrogenation catalyst, e.g. palladium on carbon, palladium black or platinum dioxide in an inert organic solvent, e.g. an alkanol containing from 1 to 4 carbon atoms such as methanol or ethanol, or ethyl acetate, or a mixture of two or more of them, at laboratory temperature at normal or elevated pressure, e.g. at a hydrogen pressure from atmospheric to 15 kg/cm$^2$.

The pyridine derivatives of general formula I, wherein B is other than oxygen and sulphur atoms, Z represents an ethynylene group, $R^1$ represents a grouping of the formula: —COOR$^4$, in which $R^4$ represents a hydrogen atom, or an alkyl group containing from 1 to 12 carbon atoms, and the other symbols are as hereinbefore defined, i.e. compounds of the general formula:

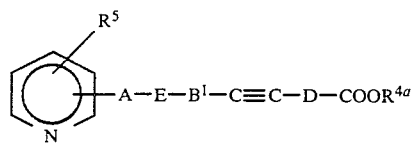

IC (wherein the various symbols are as hereinbefore defined) are prepared by dehydrohalogenation (i.e. dehydrobromination or dehydrochlorination) of compounds of general formula IA, wherein $R^2$ represents a hydrogen atom, $R^3$ represents a bromine or chlorine atom, and the other symbols are as hereinbefore defined, i.e. compounds of the general formula:

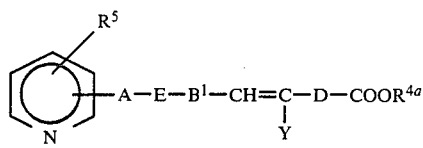

ID (wherein Y represents a bromine or chlorine atom, and the other symbols are as hereinbefore defined).

The dehydrohalogenation may be carried out with a known dehydrohalogenation reagent, for example a bicycloamine such as DBU(i.e. 1,5-diazabicyclo[5.4.0.]undecene-5), DBN(i.e. 1,5-diazabicyclo[4.3.0.]nonene-5) or DABCO(i.e. 1,4-diazabicyclo[2.2.2]octane), or an alkali metal, e.g. sodium or potassium, alkoxide containing from 1 to 4 carbon atoms. The reaction may be carried out at a temperature of 110° C. to ambient, preferably at a temperature of 80° C. to ambient and (1) when the reagent is a bicycloamine, in the absence or presence of an inert organic solvent, e.g. toluene, benzene, DMSO or dioxane, or (2) when the reagent is an alkoxide, in the presence of an inert organic solvent, e.g. an alkanol containing from 1 to 4 carbon atoms such as methanol, ethanol or tert-butanol, or N,N-dimethylformamide.

The pyridine derivatives of general formula I, wherein B represents an oxygen or sulphur atom, Z represents a single bond, D represents an alkylene group containing from 1 to 5 carbon atoms, $R^1$ represents a grouping of the formula: —COOR$^4$, in which $R^4$ represents an alkyl group containing from 1 to 12 carbon atoms, and the other symbols are as hereinbefore defined, i.e. compounds of the general formula:

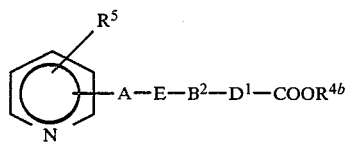

IE (wherein $B^2$ represents an oxygen or sulphur atom, and the other symbols are as hereinbefore defined) are prepared by reaction of metal salts of compounds of the general formula:

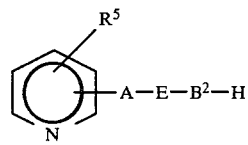

VI (wherein the various symbols are as hereinbefore defined) with halogen compounds of the general formula:

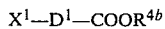

VII (wherein $X^1$ represents a halogen atom, and the other symbols are as hereinbefore defined).

The reaction may be carried out in an inert organic solvent, e.g. tetrahydrofuran, diethyl ether, dioxane, benzene, toluene, xylene, hexane, acetone, acetonitrile, N,N-dimethylformamide, hexamethylphosphoramide(HMPA), or a mixture of two or more of them, at a temperature of −78° C. to the reflux temperature of the reaction mixture, preferably at a temperature from ambient to the reflux temperature of the reaction mixture.

The metal salts may be prepared from compounds of general formula VI by reaction with a base, for example a lithioating reagent such as butyllithium, an alkali metal hydroxide such as potassium or sodium hydroxide, an alkali metal alkoxide such as potassium or sodium methoxide or butoxide, an alkali metal carbonate such as potassium or sodium carbonate, or an alkali metal hydride such as potassium or sodium hydride, in an inert organic solvent, e.g. tetrahydrofuran, diethyl ether, dioxane, benzene, toluene, xylene, hexane, acetone, acetonitrile, N,N-dimethylformamide, HMPA, methanol, ethanol, or a mixture of two or more of them, at a temperature of −78° to 100° C.

The metal salts may be used as the reaction mixture without isolation.

Halogen compounds of general formula VII may be prepared by methods known per se.

The pyridine derivatives of general formula I, wherein A represents an alkylene group containing from 1 to 5 carbon atoms, $R^1$ represents a grouping of the formula: $-COOR^4$, in which $R^4$ represents a hydrogen atom, or an alkyl group containing from 1 to 12 carbon atoms, B is other than oxygen and sulphur atoms, and the other symbols are as hereinbefore defined, i.e. compounds of the general formula:

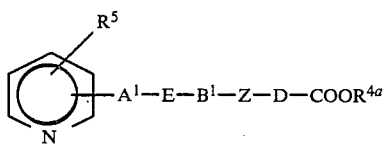

IF (wherein $A^1$ represents an alkylene group containing from 1 to 5 carbon atoms, and the other symbols are as hereinbefore defined) are prepared by oxidation of compounds of the general formula:

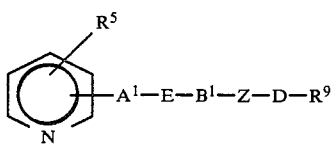

VIII (wherein $R^9$ represents a formyl or hydroxymethyl group, and the other symbols are as hereinbefore defined), followed, if desired, by esterification.

The oxidation for the conversion of a formyl or hydroxymethyl group to a carboxy group is well known. For example, the methods are described in 'Compendium of Organic Synthetic Methods', Volume 1(1971), 2(1974) or 3(1977), Section 19(in the case of a formyl group) or 18(in the case of a hydroxymethyl group), John Wiley & Sons, Inc. (USA) (hereinafter referred to as the Reference A). Advantageously, the oxidation may be carried out by using Johns reagent, or by the method described in J. Amer. Chem. Soc., 90, 5616(1968).

Compounds of general formula IF also are prepared by hydrolysis of compounds of the general formula:

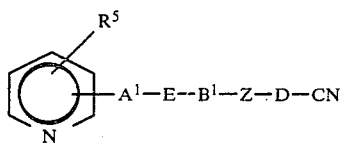

IX (wherein the various symbols are as hereinbefore defined), followed, if desired, by esterification.

The hydrolysis for the conversion of a nitrile group to a carboxy group is well known. For example, the methods are described in the aforementioned Reference A, Section 28. Advantageously, the hydrolysis may be carried out with conc-hydrochloric acid at 80° to 90° C.

The esterification is as hereafter described.

The pyridine derivatives of general formula I, wherein $R^1$ represents a grouping of the formula: $-COOR^4$, in which $R^4$ represents a hydrogen atom, or an alkyl group containing from 1 to 12 carbon atoms, D represents an alkylene group containing from 2 to 5 carbon atoms branched at α-position of the carboxy group, B is other than oxygen and sulphur atoms, A represents an alkylene group containing from 1 to 5 carbon atoms, and the other symbols are as hereinbefore defined, i.e. compounds of the general formula:

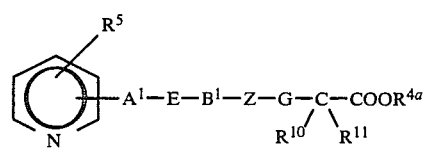

IG (wherein G represents a single bond, or an alkylene group containing from 1 to 3 carbon atoms, $R^{10}$ represents an alkyl group containing from 1 to 4 carbon atoms, $R^{11}$ represents a hydrogen atom, or an alkyl group containing from 1 to 4 carbon atoms, and the other symbols are as hereinbefore defined, with the proviso that the total carbon number of the group

is an integer of 2 to 5) are prepared by reaction of compounds of the general formula:

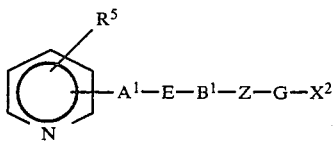

X (wherein $X^2$ represents a halogen atom, and the other symbols are as hereinbefore defined) with lithium compounds of compounds of the general formula:

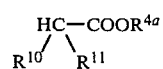

XI (wherein the various symbols are as hereinbefore defined) in an inert organic solvent, e.g. tetrahydrofuran, diethyl ether, hexane, HMPA, or a mixture of two or more of them, at a temperature of −78° C. to ambient.

The lithium compounds may be prepared from compounds of general formula XI with a lithioating reagent such as lithium diisopropylamide by methods known per se.

The pyridine derivatives of general formula I, wherein a grouping —B—Z—D— represents a single bond, $R^1$ represents a grouping of the formula: —COOR$^4$, in which $R^4$ represents an alkyl group containing from 1 to 12 carbon atoms, A represents a grouping of the formula:

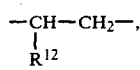

in which $R^{12}$ represents a hydrogen atom, or an alkyl group containing from 1 to 3 carbon atoms, and the other symbols are as hereinbefore defined, i.e. compounds of the general formula:

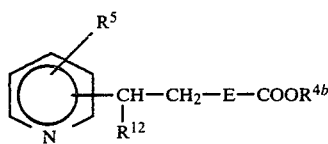

IH (wherein the various symbols are as hereinbefore defined) are prepared by hydrogenation of compounds of the general formula:

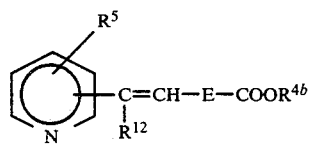

XII (wherein the double bond is E or Z, or their mixture, and the other symbols are as hereinbefore defined) by means heretofore mentioned for the conversion of compounds of general formula IA to those of general formula IB.

The pyridine derivatives of general formula I, wherein A represents an alkylene group containing from 1 to 5 carbon atoms, $R^1$ represents a grouping of the formula: —COOR$^4$, in which $R^4$ represents a hydrogen atom, or an alkyl group containing from 1 to 12 carbon atoms, and the other symbols are as hereinbefore defined, i.e. compounds of the general formula:

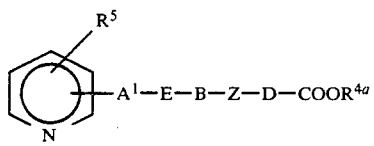

IJ (wherein the various symbols are as hereinbefore defined) are prepared by halogenation or acetylation of a hydroxy group of compounds of the general formula:

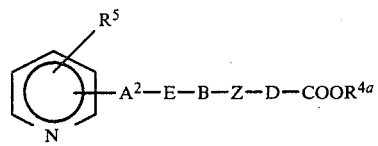

IK (wherein $A^2$ represents an alkylene group containing from 1 to 5 carbon atoms substituted by a hydroxy group, and the other symbols are as hereinbefore defined), followed by dehalogenation or deacetoxylation of the compounds obtained above.

The halogenation may be carried out by the methods as described in Section 138 of the Reference A, preferably the halogenation may be efected by using thionyl chloride in the absence or presence of an inert organic solvent, e.g. benzene, chloroform, dioxane, tetrahydrofuran, toluene, xylene, or a mixture of two or more of them, at a temperature of 100° C. to ambient, preferably at 40° to 80° C.

The acetylation may be carried out by using acetyl chloride or acetic anhydride in an inert organic solvent, e.g. methylene chloride or pyridine, in the presence of a tertiary amine, e.g. pyridine or triethylamine, at a temperature below ambient.

The dehalogenation may be carried out by the methods as described in Section 160 of the Reference A, preferably the dehalogenation (especially dechlorination) may be effected by using zinc powder and acetic acid at ambient temperature.

The deacetoxylation may be carried out by reaction with zinc powder and acetic acid at ambient temperature.

Compounds of general formula IJ, wherein B is other than a sulphur atom, Z is other than an ethynylene group and a grouping of the formula:

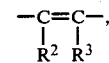

and the other symbols are as hereinbefore defined, may be prepared by reduction of compounds of general formula IK, wherein B is other than a sulphur atom, Z is other than an ethynylene group and a grouping of the formula:

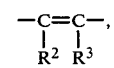

and the other symbols are as hereinbefore defined.

The suitable reduction may be carried out under an atmosphere of hydrogen with a catalyst, e.g. palladium on carbon, palladium black or platinum dioxide, in acetic acid or trifluoroacetic acid at ambient temperature at normal or elevated pressure, e.g. at a hydrogen pressure from atmospheric to 15 kg/cm$^2$.

The pyridine derivatives of general formula I, wherin D represents an alkylene group containing from 1 to 5 carbon atoms, $R^1$ represents a hydroxy group, and the other symbols are as hereinbefore defined, i.e. compounds of the general formula:

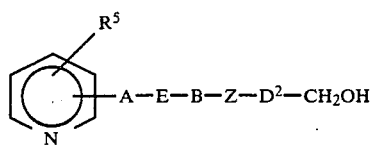 IL (wherein $D^2$ represents a single bond, or an alkylene group containing from 1 to 4 carbon atoms, and the other symbols are as hereinbefore defined) are prepared from compounds of the general formula:

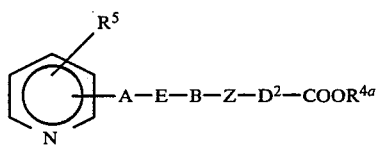 IM (wherein the various symbols are as hereinbefore defined) or compounds of the general formula:

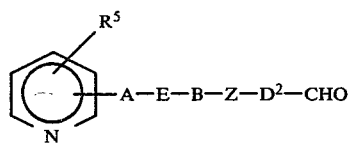 XIII (wherein the various symbols are as hereinbefore defined) by reduction the carboxy or ester group —$COOR^{4a}$ or the formyl group —CHO to a hydroxymethyl group —$CH_2OH$.

The suitable reduction for the conversion of a carboxy, ester or formyl group to a hydroxymethyl group are well known. For example the reduction is described in Section 32 (in the case of a carboxy group), 38 (in the case of an ester) and 34 (in the case of a formyl group) of the Reference A. Advantageously, the reduction of compounds of general formula IM or XIII may be effected by using lithium aluminium hydride or diisobutylaluminium hydride in an inert organic solvent, e.g. tetrahydrofuran, diethyl ether, 1,2-dimethoxyethane, diglyme, hexane, pentane, benzene, toluene, or a mixture of two or more of them, at a temperature of −78° C. to ambient. The reduction of compounds of general formula XIII may be effected by using sodium borohydride, potassium borohydride, lithium borohydride, zinc borohydride, lithium tri-tert-butoxyaluminium hydride, lithium trimethoxyaluminium hydride, sodium cyanoborohydride, potassium tri-sec-butylborohydride or lithium aluminium hydride-quinine in an inert organic solvent, e.g. an alkanol containing from 1 to 4 carbon atoms such as methanol, ethanol or isopropanol, or an ether such as tetrahydrofuran, dioxane, 1,2-dimethoxyethane, or a mixture of two or more of them, at a temperature of −78° C. to ambient.

The pyridine derivatives of general formula I, wherein $R^1$ represents a hydroxy group, D represents an alkylene group containing from 2 to 5 carbon atoms branched at α-position of the hydroxy group, and the other symbols are as hereinbefore defined, i.e. compounds of the general formula:

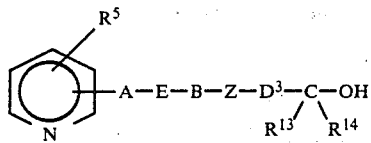 IN (wherein $D^3$ represents a single bond, or an alkylene group containing from 1 to 3 carbon atoms, $R^{13}$ represents an alkyl group containing from 1 to 4 carbon atoms, $R^{14}$ represents a hydrogen atom, or an alkyl group containing from 1 to 4 carbon atoms, and the other symbols are as hereinbefore defined, with the proviso that the total carbon number of the group

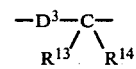

is an integer of 2 to 5) are prepared by alkylation of compounds of the general formula:

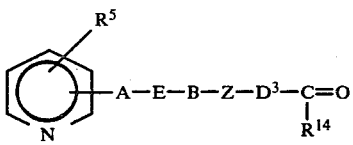 XIV (wherin the various symbols are as hereinbefore defined).

The alkylation may be carried out by using an organometallic compound of the general formula:

$R^{13}$—Met      XV (wherein Met represents a lithium atom or a magnesium halide group, and $R^{13}$ is an hereinbefore defined) in an inert organic solvent, e.g. diethyl ether, tetrahydrofuran, hexane, or a mixture of two or more of them, at a temperature of −78° C. to ambient, or by using an aluminium compound of the general formula:

$(R^{13})_3Al$ (wherein $R^{13}$ is as hereinbefore defined) by the method described in J. Amer. Chem. Soc., 96, 5865(1974).

Compounds of general formula IN, wherein $R^{14}$ hydrogen atom, and the other symbols are as hereinbefore defined, may be prepared from compounds of general formula XIV, wherein $R^{14}$ is other than a hydrogen atom, by means heretofore mentioned for the conversion of compounds of general formula XIII to those of general formula IL.

The pyridine derivatives of general formula I, wherein $R^1$ represents a hydroxy group, the group —V—Z—D— represents a single bond, and the other symbols are as hereinbefore defined, i.e. compounds of the general formula:

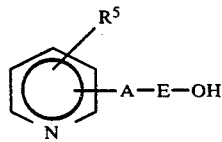 IO (wherein the various symbols are as hereinbefore defined) are prepared by reaction of compounds of the general formula:

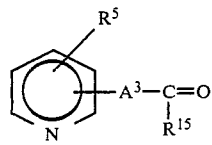

XVII (wherein $A^3$ represents a single bond, or an alkylene group containing from 1 to 4 carbon atoms, $R^{15}$ represents a hydrogen atom, or an alkyl group containing from 1 to 4 carbon atoms, and $R^5$ is as hereinbefore defined) with an organometallic compound of the general formula:

Met—$A^4$—E—O—Met   XVIII (wherein $A^4$ represents a single bond, or an alkylene group containing from 1 to 4 carbon atoms, and the other symbols are as hereinbefore defined) by means heretofore mentioned for the converion of compounds of general formula XV to those of general formula IN, followed, if desired, by elimination reaction of the obtained hydroxy group of compounds of the general formula:

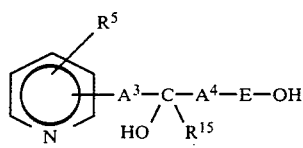

IP (wherein the various symbols are as hereinbefore defined, with the proviso that the total carbon number of $A^3$, $A^4$ and $R^{15}$ is zero, or an integer of 1 to 4) by means heretofore mentioned for the conversion of compounds of general formula IK to those of general formula IJ.

Organometallic compounds of general formula XVIII may be prepared from a compound of the general formula:

$X^3$—$A^4$—E—OH   XIX (wherein $X^3$ represents a halogen atom, and the other symbols are as hereinbefore defined) by methods known per se.

Compounds of general formula XIX may be prepared by methods known per se.

Starting materials of general formula II may be prepared by the series of reactions depicted schematically below in Scheme A, wherein $X^4$ represents a halogen atom, L represents a carbonyl-protecting group, and the other symbols are as hereinbefore defined.

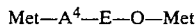

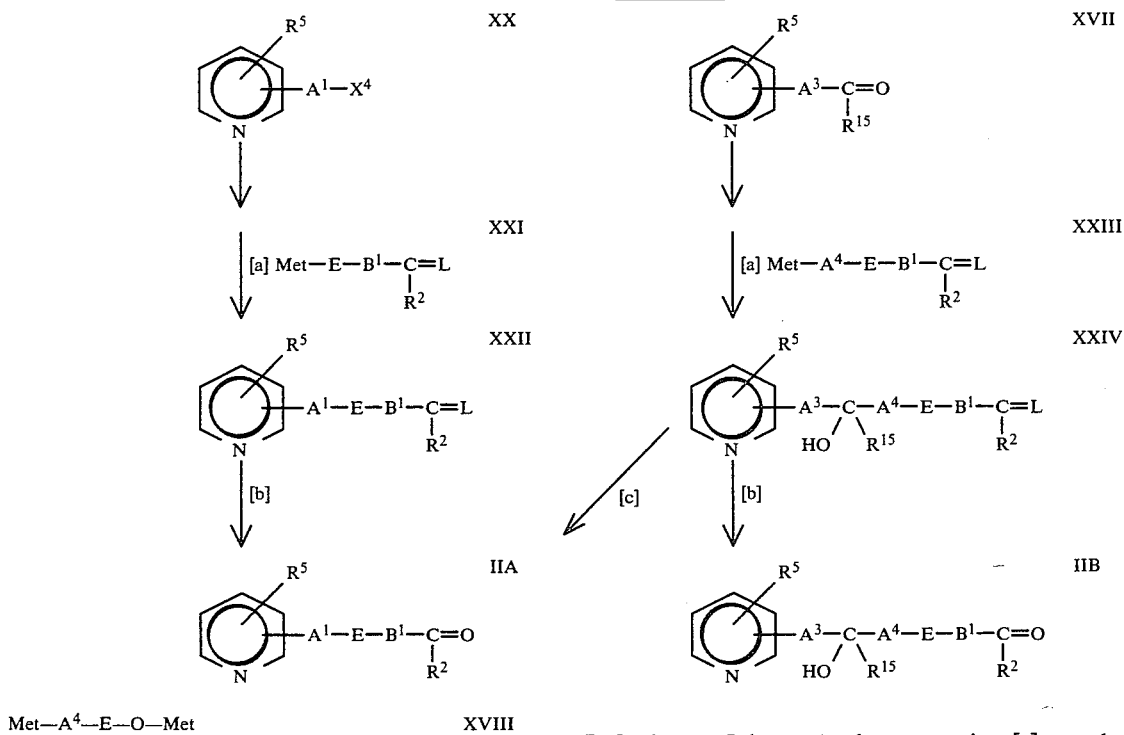

Referring to Scheme A, the conversion [a] may be carried out by means heretofore mentioned for the conversion of compounds of general formula XV to those of general formula IN. The conversion [b] may be carried out by methods known per se for the conversion of a protected carbonyl group to a carbonyl group. For example, when L represents an ethylenedioxy, dimethoxy or diethoxy group, the conversion may be carried out under acidic conditions, for example by reaction with hydrochloric acid in tetrahydrofuran at ambient temperature. The conversion [c] may be carried out by means heretofore mentioned for the conversion of compounds of general formula IK to those of general formula IF.

Compounds of general formula XVII, XX, XXI and XXIII may be prepared by methods known per se.

Starting materials of general formula VIII, wherein $R^9$ represents a formyl group, and formula XIII and XIV may be prepared from the corresponding compounds by the procedure as described in Scheme A.

Starting materials of general formula VI, wherein $B^2$ represents a sulphur atom, may be prepared from compounds of the general formula:

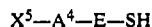

$$X^5—A^4—E—SH \qquad XXV$$

(wherein $X_5$ represents a halogen atom, and the other symbols are as hereinbefore defined), which may be prepared by methods know per se, by means heretofore mentioned for the conversion of compounds of general formula XIX to those of general formula IO.

Starting materials of general formula VIII, wherein $R^9$ represents a hydroxymethyl group, may be prepared by means heretofore mentioned for the conversion of compounds of general formula XIII to those of general formula IL.

Starting materials of general formula IX may be prepared from compounds of the general formula:

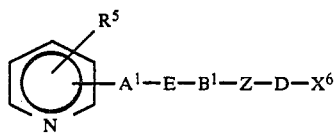

XXVI (wherein $X^6$ represents a halogen atom, and the other symbols are as hereinbefore defined) by the methods as described in section A 190 of the Reference A, for example by using sodium or potassium cyanide in DMSO.

Compounds of general formula XXVI, wherein the group $—B^1—Z—D—$ represents a single bond, may be prepared from compounds of the general formula:

$$X^7—A^1—E—X^6 \qquad XXVII$$

(wherein $X^7$ represents a halogen atom, and the other symbols are as hereinbefore defined) by reaction with lithium aluminium salt of pyridine (prepared from pyridine and lithium aluminium hydride).

Compounds of general formula XXVII, wherein the group $—B^1—Z—D—$ is other than a single bond, may be prepared by reaction of compounds of the general formula:

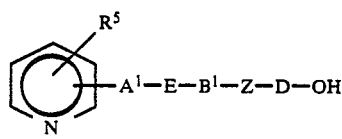

IQ (wherein the various symbols are as hereinbefore defined, with the proviso that the group $—B^1—Z—D—$ is other than a single bond) by means heretofore mentioned for the conversion of compounds of general formula IK to those of general formula IJ. Starting materials of general formula X may also be prepared by the procedure as described above.

Starting materials of general formula XII may be prepared by the Wittig reaction of compounds of the general formula:

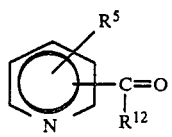

XXVIII

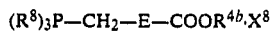

(wherein the various symbols are as hereinbefore defined) with phosphonium compounds of the general formula:

$$(R^8)_3P—CH_2—E—COOR^{4b}.X^8 \qquad XXIX$$

(wherein $X^8$ represents a halogen atom, and the other symbols are as hereinbefore defined) by means heretofore mentioned for the preparation of compounds of general formula IA.

Compounds of general formula XXVIII and XXIX may be prepared by methods known per se.

The pyridine derivatives of general formula I, wherein $R^1$ represents a grouping of the formula: $—COOR^4$ or $—COSR^4$, in which $R^4$ is other than a hydrogen atom, and the other symbols are as hereinbefore defined, are prepared by esterification of acids of general formula I, wherein $R^4$ represents a carboxy group, and the other symbols are as hereinbefore defined, by methods know per se, for example, when $R^1$ represents a grouping of the formula: $—COOR^4$, in which $R^4$ is an alkyl group, by reaction with (1) a diazoalkane or (2) an N,N-dimethylformamidedialkyl acetal, or when $R^1$ represents a grouping of the formula: $—COOR^4$, in which $R^4$ is an alkyl or aralkyl group, by reaction with (3) an alkyl or aralkyl halide, or when $R^1$ represents a grouping of the formula: $—COOR^4$ or $—COSR^4$, in which $R^4$ is an alkyl or aralkyl group or any other esterifying groups within the definition of $R^4$, (4) using dicyclohexylcarbodiimide (by the procedure described in our Japanese Pat. No. 762305), (5) using a pivaloyl halide (by the procedure described in our British Pat. No. 1364125), (6) using an arylsulphonyl or alkylsulphonyl halide (by the procedure described in our British Pat. No. 1362956), (7) using isobutyl chloroformate (by the procedure described in British Pat. No. 1492439) or (8) using dipryridyl disulphide and triphenylphosphine [by the procedure described in "Tetrahedron Letters", 3409(1976)].

The preparation of esters using a diazoalkane is carried out by reacting the corresponding acid with an appropriate diazoalkane in an inert organic solvent, e.g. diethyl ether, ethyl acetate, methylene chloride, acetone, methanol, or a mixture of two or more of them, at a temperature from ambient to $-10°$ C., preferably at $0°$ C.

The preparation of esters using an N,N-dimethylformamide-dialkyl acetal is carried out by reacting the corresponding acid with an N,N-dimethylformamide-dialkyl acetal, e.g. N,N-dimethylformamide-dimethyl acetal, in anhydrous benzene [cf. Helv. Chem. Acta, 48, 1746(1965)].

The preparation of esters using an alkyl or aralkyl halide, e.g. methyl iodide, butyl bromide, decyl bromide, benzyl chloride or biphenylmethyl bromide, (i) in acetone in the presence of an alkali metal, e.g. potassium or sodium, carbonate [cf. J. Org. Chem., 34, 3717(1969)], (ii) in N,N-dimethylacetamide or N,N-dimethylformamide in the presence of an alkali metal, e.g. potassium or sodium, bicarbonate [cf. Advan. Org. Chem., 5, 37(1965)], (iii) in dimethyl sulphoxide in the presence of calcium oxide [cf. Synthesis, 262(1972)] or (iv) in N,N-dimethylacetamide or N,N-dimethylformamide in the presence of tetramethylammonium hydroxide [cf. Synthetic Comm., 2, 215(1972)], at a temperature of $0°$ C. to ambient.

The preparation of esters using dicyclohexylcarbodiimide is carried out by reacting the corresponding acid with an appropriate alcohol R⁴OH, wherein R⁴ is other than a hydrogen atom, or thiol R⁴SH, wherein R⁴ is other than a hydrogen atom, in an inert organic solvent such as a halogenated hydrocarbon, e.g. chloroform or methylene chloride, in the presence of a base such as pyridine or picoline, preferably pyridine, at a temperature of 0° C. to ambient.

The preparation of esters using a pivaloyl, arylsulphonyl or alkylsulphonyl halide or isobutyl chloroformate is carried out by reacting the corresponding acid with a tertiary amine, e.g. triethylamine or pyridine, and a pivaloyl halide, e.g. pivaloyl chloride, arylsulphonyl halide, e.g. p-toluenesulphonyl chloride or benzenesulphonyl chloride, alkylsulphonyl halide, e.g. methanesulphonyl chloride or ethanesulphonyl chloride, or isobutyl chloroformate, in the presence or absence of an inert organic solvent such as a halogenated hydrocarbon, e.g. chloroform or methylene chloride, or an ether, e.g. diethyl ether or tetrahydrofuran, to prepare a mixed acid anhydride of the acid, and adding thereto, at a temperature of 0° C. to ambient, an alcohol R⁴OH, wherein R⁴ is other than a hydrogen atom, or thiol R⁴SH, wherein R⁴ is other than a hydrogen atom to obtain the desired ester.

The preparation of esters using dipyridyl disulphide and triphenylphosphine is carried out by reacting the corresponding acid with an appropriate alcohol R⁴OH, wherein R⁴ is other than a hydrogen atom, or thiol R⁴SH, wherein R⁴ is other than a hydrogen atom, in an inert organic solvent, e.g. toluene, benzene or xylene, at a temperature from ambient to 80° C.

Acids or thioacids of pyridine derivatives of general formula I, wherein $R^1$ represents a grouping of the formula: —COOR⁴ or —COSR⁴, in which R⁴ represents a hydrogen atom, and the other symbols are as hereinbefore defined, may be prepared by saponification of the corresponding ester of general formula I, wherein $R^1$ represents a grouping of the formula: —COOR⁴ or —COSR⁴, in which R⁴ is other than a hydrogen atom, and the other symbols are as hereinbefore defined, by methods known per se. For example, methods for the saponification are described in Section 23 of the Reference A, advantageously, the saponification may be effected by using an aqueous solution of an alkali metal, e.g. sodium, potassium or lithium, hydroxide or carbonate, or an alkaline earth metal, e.g. calcium or barium, hydroxide or carbonate in the absence or presence of a water miscible solvent such as an ether, e.g. dioxane or tetrahydrofuran, or an alkanol containing from 1 to 4 carbon atoms, e.g. methanol or ethanol, at a temperature of −10° to 100° C., preferably at ambient temperature, or using an anhydrous solution of alkali metal, e.g. sodium, potassium or lithium, hydroxide or carbonate in an anhydrous alkanol containing from 1 to 4 carbon atoms, e.g. absolute methanol or ethanol, at a temperature of −10° to 100° C., preferably at ambient temperature.

Compounds of general formula I, wherein $R^1$ represents a grouping of the formula: —COOR⁴ or —COSR⁴, in which R⁴ represents a hydrogen atom, may, if desired, be converted by methods known per se into salts. Preferably, the salts are non-toxic salts. By the term 'non-toxic salts', as used in this specification, is meant salts the cations (or in the case of acid addition salts referred to hereinafter the anions) of which are relatively innocuous to the animal organism when used in therapeutic doses so that the beneficial pharmacological properties of the compounds of general formula I are not vitiated by side-effects ascribable to those cations (or anions). Preferably the salts are water-soluble. Suitable non-toxic salts include the alkali metal, e.g. sodium or potassium, salts, the alkaline earth metal, e.g. calcium or magnesium, salts and ammonium salts, and pharmaceutically acceptable (i.e. non-toxic) amine salts. Amines suitable for forming such salts with carboxylic acids or carbothioic S-acids are well known and include, for example, amines derived in theory by the replacement of one or more of the hydrogen atoms of ammonia by groups, which may be the same or different when more than one hydrogen atom is replaced, selected from, for example alkyl groups containing from 1 to 6 carbon atoms and hydroxyalkyl containing 2 to 3 carbon atoms. Suitable non-toxis amine salts are, e.g. tetraalkylammonium salts such as tetramethylammonium salts, and other organic amine salts such as methylamine salts, dimethyamine salts, cyclopentylamine salts, benzylamine salts, phenethylamine salts, piperidine salts, monoethanolamine salts, diethanolamine salts, lysine salts and arginine salts.

Salts may be prepared from the acids or thioacids of general formula I, wherein $R^1$ represents a grouping of the formula: —COOR⁴ or —COSR⁴, in which R⁴ represents a hydrogen atom, by methods known per se, for example by reaction of stoichiometric quantities of an acid or thiocid of general formula I and the appropriate base, e.g. an alkali metal or alkaline earth metal hydroxide or carbonate, ammonium hydroxide, ammonia or an organic amine, in a suitable solvent. The salts may be isolated by lyophilisation of the solution or, if sufficiently insoluble in the reaction medium, by filtration, if necessary after removal of part of the solvent.

The pyridine derivative of general formula I may, if desired, be converted by methods know per se into acid addition salts, which are preferably non-toxic as hereinbefore defined. Suitable non-toxic acid addition salts are the salts with inorganic acids such as hydrochloric acid, hydrobromic acid, hydroiodic acid, sulphuric acid, phosphoric acid and nitric acid, and with organic acids such as acetic acid, propionic acid, lactic acid, tartaric acid, citric acid, methanesulphic acid, ethanesulphonic acid, benzenesulphonic acid, toluenesulphonic acid, isethionic acid and succinic acid.

Acid addition salts may be prepared from the compounds of general formula I by methods know per se, for example by reaction of stoichiometric quantities of a compound of general formula I and the appropriate acid, e.g. an inorganic acid such as hydrochloric acid, hydrobromic acid, hydroiodic acid, sulphuric acid, phosphoric acid or nitric acid, or an organic acid such as acetic acid, propionic acid, lactic acid, tartaric acid, citric acid, methanesulphonic acid, ethanesulphonic acid, benzenesulphonic acid, toluenesulphonic acid, isethionic acid or succinic acid, in a suitable solvent. The acid addition salts may be purified by recrystallisation from a suitable solvent or suitable mixture of two or more solvents.

The pyridine derivatives of general formula I of the present invention exhibit an inhibitory activity on thromboxane synthetase from rabbit platelet microsomes. That is, the pyridine derivatives of this invention inhibit conversion of prostaglandin $H_2$ into thromboxane $B_2$ via thromboxane $A_2$ which is an unstable intermidiate, and which is known to induce irreversible platelet aggregation and to contract smooth muscle and particularly a blood vessel muscle [Nature, 261(6), 17(1976d)]. These results demonstrate that the pyridine derivatives of this invention inhibit the biosynthesis of thromboxane $A_2$, and are thus useful for the treatment or prevention of diseases caused by thromboxane $A_2$, such as inflammation, hypertension, thrombus, cerebral apoplexy, asthma, myocardial infarction, cardiostenosis, cerebral infarction and acute cardiac death.

The inhibitory activity of the pyridine derivatives of this invention can be confirmed by determination of the thromboxane $B_2$ produced by thromboxane synthetase from prostaglandin $H_2$ via thromboxane $A_2$. Furthermore, the inhibitory activity of the pyridine derivatives of this invention can be confirmed by determination of the inhibitory effect on platelet aggregation caused by arachidonic acid (arachidonic acid is converted to prostaglandin $H_2$ by cyclooxygenase, and prostaglandin $H_2$ is converted to thromboxane $B_2$ via thromboxane $A_2$ which is known to induce platelet aggregation as described above). Further still, the inhibitory action of the pyridine derivatives of this invention can be confirmed by determination of the inhibitory effect on sudden deaths caused by arachidonic acid.

For example, in standard laboratory tests, (Z)-2-bromo-3-[4-(3-pyridylmethyl)phenyl]acrylic acid methyl ester, 4-(3-pyridylmethyl)-phenylacetic acid hydrochloride, 4-(3-pyridylmethyl)phenol hydrochloride, 4-(3-pyridylmethyl)phenoxyacetic acid ethyl ester, 2-[4-(3-pyridylmethyl)phenoxy]propionic acid ethyl ester, (E)-2-methyl-3-[3-methyl-4-(3-pyridylmethyl)phenyl]acrylic acid ethyl ester, (E)-2-methyl-3-[3-(3-pyridylmethyl)phenyl]acrylic acid ethyl ester, 3-[4(3-pyridylmethyl)phenyl]propionic acid ethyl ester, 2-methyl-3-[4-(3-pyridylmethyl)phenyl]propionic acid ethyl ester, (E)-3-[4-(3-pyridylmethyl)phenyl]acrylic acid hydrochloride, 3-[4-(3-pyridylmethyl)phenyl]propionic acid hydrochloride, (E)-2-methyl-3-[4-(3-pyridylmethyl)phenyl]acrylic acid hydrochloride, 2-methyl-3-[4-(3-pyridylmethyl)phenyl]propionic acid hydrochloride, (Z)-2-bromo-3-[4-(3-pyridylmethyl)phenyl]acrylic acid hydrochloride, 4-(3-pyridylmethyl)benzoic acid hydrochloride, 2,2-dimethyl-3-[4-(3-pyridylmethyl)phenyl]propionic acid hydrochloride, (E)-2-ethyl-3-[4-(3-pyridylmethyl)phenyl]acrylic acid hydrochloride, (E)-3-[4-(3-pyridylhydroxymethyl(-phenyl]acrylic acid hydrochloride, (E)-2-methyl-3[4-(1-3'-pyridylethyl)phenyl]acrylic acid hydrochloride, (E)-2-methyl-3[4-(4-methyl-3-pyridylmethyl)phenyl]acrylic acid hydrochloride, (E)-5-(3-pyridylmethyl)-2-(2-carboxyvinyl)thiophene hydrochloride, (E)-5-(3-pyridylmethyl)-2-(2-carboxy-1-propenyl)thiophene hydrochloride, (E)-3-[4-(3-pyridylmethyl)phenyl]-2-butenoic acid hydrochloride, 2-[4-(3-pyridylmethyl)phenoxy]acetic acid hydrochloride, 2-[4-(3-pyridylmethyl)phenoxy]propionic acid hydrochloride, 2-methyl-2-[4-(3-pyridylmethyl)phenoxy]propionic acid hydrochloride, (E)-2-methyl-3-[3-methyl-4-(3-pyridylmethyl)phenyl]acrylic acid hydrochloride, (E)-3-[3-methyl-4-(3-pyridylmethyl)phenyl]acrylic acid hydrochloride, (E)-2-methyl-3-[3-(3-pyridylmethyl)phenyl]acrylic acid hydrochloride, 2-methyl-2-[4-(3-pyridylmethyl)phenylthio]propionic acid hydrochloride, 2-methyl-3-[4-(1-3'-pyridylmethyl)phenyl]propionic acid hydrochloride, 3-[4-(3-pyridylmethyl)phenyl]butyric acid hydrochloride, (E)-2-methyl-3-[4-(3-pyridylmethyl)phenyl]acrylic acid, (E)-2-methyl-3-[4-(3-pyridylmethyl)phenyl]acrylic acid benzyl ester, (E)-2-methyl-3-[4-(3-pyridylmethyl)-phenyl]acrylic acid biphenylmethyl ester, (E)-2-methyl-3-[4-(3-pyridylmethyl)phenyl]acrylic acid phenyl ester, (E)-2-methyl-3-[4-(3-pyridylmethyl)phenyl]acrylic acid 3-trifluoromethylphenyl ester, (E)-2-methyl-3-[4-(3-pyridylmethyl)phenyl]acrylic acid 2-methylphenyl ester, (E)-2-methyl-3-[4-(3-pyridylmethyl)phenyl]thioacrylic S-acid S-ethyl ester hydrochloride, (E)-2-methyl-3-[4-(3-pyridylmethyl)phenyl]acrylic acid mesylate and (E)-2-methyl-3-[4-(3-pyridylmethyl)phenyl]acrylic acid sodium salt produce a 50% inhibition of thromboxane synthetase from rabbit platelet microsomes at the molar concentrations from $3\times10^{-9}$ to $6.5\times10^{-7}$.

Preferred pyridine derivatives of the present invention are as follows:

4-(3-pyridylmethyl)benzoic acid,
4-(3-pyridylmethyl)phenylacetic acid,
3-[4-(3-pyridylmethyl)phenyl]propionic acid,
4-[4-(3-pyridylmethyl)phenyl]butyric acid,
5-[4-(3-pyridylmethyl)phenyl]valeric acid,
6-[4-(3-pyridylmethyl)phenyl]hexanoic acid,
7-[4-(3-pyridylmethyl)phenyl]heptanoic acid,
8-[4-(3-pyridylmethyl)phenyl]octanoic acid,
9-[4-(3-pyridylmethyl)phenyl]nonanoic acid,
10-[4-(3-pyridylmethyl)phenyl]decanoic acid,
3-[4-(3-pyridylmethyl)phenyl]acrylic acid,
4-[4-(3-pyridylmethyl)phenyl]-2-butenoic acid,
5-[4-(3-pyridylmethyl)phenyl]-2-pentenoic acid,
6-[4-(3-pyridylmethyl)phenyl]-2-hexenoic acid,
7-[4-(3-pyridylmethyl)phenyl]-2-heptenoic acid,
3-[4-(3-pyridylmethyl)phenyl]propynoic acid,
4-[4-(3-pyridylmethyl)phenyl]-2-butynoic acid,
5-[4-(3-pyridylmethyl)phenyl]-2-pentynoic acid,
6-[4-(3-pyridylmethyl)phenyl]-2-hexynoic acid,
7-[4-(3-pyridylmethyl)phenyl]-2-heptynoic acid,
2-methyl-3-[4-(3-pyridylmethyl)phenyl]propionic acid,
2,2-dimethyl-3-[4-(3-pyridylmethyl)phenyl]propionic acid,
2-methyl-3-[4-(3-pyridylmethyl)phenyl]butyric acid,
3-[4-(3-pyridylmethyl)phenyl]butyric acid,
2-ethyl-3-[4-(3-pyridylmethyl)phenyl]propionic acid,
3-[4-(3-pyridylmethyl)phenyl]valeric acid,
2-bromo-3-[4-(3-pyridylmethyl)phenyl]propionic acid,
2-chloro-3-[4-(3-pyridylmethyl)phenyl]propionic acid,
2-methyl-3-[4-(3-pyridylmethyl)phenyl]acrylic acid,
2-ethyl-3-[4-(3-pyridylmethyl)phenyl]acrylic acid,
3-[4-(3-pyridylmethyl)phenyl]-2-butenoic acid,
3-[4-(3-pyridylmethyl)phenyl]-2-pentenoic acid,
2-methyl-3-[4-(3-pyridylmethyl)phenyl]-2-butenoic acid,
2-bromo-3-[4-(3-pyridylmethyl)phenyl]acrylic acid,
2-chloro-3-[4-(3-pyridylmethyl)phenyl]acrylic acid,
4-(3-pyridylmethyl)phenoxyacetic acid,
2-[4-(3-pyridylmethyl)phenoxy]propionic acid,
2-methyl-2-[4-(3-pyridylmethyl)phenoxy]propionic acid,
4-(3-pyridylmethyl)phenylthioacetic acid,
2-[4-(3-pyridylmethyl)phenylthio]propionic acid,
2-methyl-2-[4-(3-pyridylmethyl)phenylthio]propionic acid, the corresponding thiophene analogues, and corresponding 1-3'-pyridylethyl, 2-3'-pyridylethyl and 3-pyridylhydroxymethyl analogues, and corresponding 3-phenyl and/or 4-pyridyl analogues, and corresponding pyridine and/or phenyl analogues substituted by an alkyl group, and esters, thioesters, alcohols, non-toxic salts and non-toxic acid addition salts thereof.

Particularly preferred pyridine derivatives of the present invention are the esters:

(E)-3-[4-(3-pyridylmethyl)phenyl]acrylic acid methyl ester, (E)-3-[4-(3-pyridylmethyl)phenyl]acrylic acid ethyl ester, (E)-2-methyl-3-[4-(3-pyridylmethyl)phenyl]acrylic acid ethyl ester, (Z)-2-bromo-3-[4-(3-pyridylmethyl)phenyl]acrylic acid methyl ester, (E)-3-[4-(3-pyridylhydroxymethyl)phenyl]acrylic acid ethyl ester, (E)-2-methyl-3-[4-(1-3'-pyridylethyl)phenyl]acrylic acid ethyl ester, (E)-2-methyl-3-[4-(4-methyl-3-pyridylmethyl)phenyl]acrylic acid ethyl ester, (E)-2-methyl-3-[3-methyl-4-(3-pyridylhydroxymethyl)phenyl]acrylic acid ethyl ester, (E)-3-[3-methyl-4-(3-pyridylhydroxymethyl)phenyl]acrylic acid ethyl ester, (E)-2-methyl-3-[3-(3-pyridylhydroxymethyl)phenyl]acrylic acid ethyl ester, (E)-2-methyl-3-[3-(4-pyridylhydroxymethyl)phenyl]acrylic acid ethyl ester, (E)-5-(3-pyridylmethyl)-2-(2-ethoxycarbonylvinyl)thiophene, (E)-5-(3-pyridylmethyl)-2-(2-ethoxycarbonyl-1-propenyl)thiophene, (E)-2-methyl-3-[4-(4-pyridylhydroxymethyl)phenyl]acrylic acid ethyl ester, (E)-3-[4-(1-3'-pyridylethyl)phenyl]acrylic acid ethyl ester, (E)-2-ethyl-3-[4-(3-pyridylmethyl)phenyl]acrylic acid ethyl ester, (E)-3-[4-(3-pyridylmethyl)phenyl]-2-butenoic acid ethyl ester, 4-(3-pyridylmethyl)benzoic acid methyl ester, 2,2-dimethyl-3-[4-(3-pyridylmethyl)phenyl]propionic acid ethyl ester, 2-[4-(3-pyridylhydroxymethyl)phenylthio]propionic acid ethyl ester, 2-[4-(3-pyridylhydroxymethyl)phenylthio]acetic acid ethyl ester, 2-methyl-2-[4-(3-pyridylhydroxymethyl)phenylthio]propionic acid ethyl ester, 4-(3-pyridylmethyl)phenoxyacetic acid ethyl ester, 2-[4-(3-pyridylmethyl)phenoxy]propionic acid ethyl ester, 2-methyl-2-[4-(3-pyridylmethyl)phenoxy]propionic acid ethyl ester, (E)-2-methyl-3-[3-methyl-4-(3-pyridylmethyl)phenyl]acrylic acid ethyl ester, (E)-3-[3-methyl-4-(3-pyridylmethyl)phenyl]acrylic acid ethyl ester, (E)-2-methyl-3-[3-(3-pyridylmethyl)phenyl]acrylic acid ethyl ester, (E)-2-methyl-3-[3-(4-pyridylmethyl)phenyl]acrylic acid ethyl ester, (E)-2-methyl-3-[4-(4-pyridylmethyl)phenyl]acrylic acid ethyl ester, 2-[4-(3-pyridylmethyl)phenylthio]propionic acid ethyl ester, 2-[4-(3-pyridylmethyl)phenylthio]acetic acid ethyl ester, 2-methyl-2-[4-(3-pyridylmethyl)phenylthio]propionic acid ethyl ester, 3-[4-(3-pyridylmethyl)phenyl]propionic acid ethyl ester, 2-methyl-3-[4-(3-pyridylmethyl)phenyl]propionic acid ethyl ester, 3-[4-(3-pyridylhydroxymethyl)phenyl]propionic acid ethel ester, 2-methyl-3-[4-(1-3'-pyridylmethyl)phenyl]propionic acid ethyl ester, 3-[4-(1-3'-pyridylethyl)phenyl]propionic acid ethyl ester, 3-[4-(3-pyridylmethyl)phenyl]butyric acid ethyl ester, 4-[2-(3-pyridylethyl)]benzoic acid ethyl ester, (E)-2-methyl-3-[4-(3-pyridylmethyl)phenyl]acrylic acid decyl ester, (E)-2-methyl-3-[4-(3-pyridylmethyl)phenyl]acrylic acid benzyl ester, (E)-2-methyl-3-[4-(3-pyridylmethyl)phenyl]acrylic acid biphenylmethyl ester, (E)-2-methyl-3-[4-(3-pyridylmethyl)phenyl]acrylic acid butyl ester, (E)-2-methyl-3-[4-(3-pyridylmethyl)phenyl]acrylic acid phenyl ester, (E)-2-methyl-3-[4-(3-pyridylmethyl)phenyl]acrylic acid 3-trifluoromethylphenyl ester, (E)-2-methyl-3-[4-(3-pyridylmethyl)phenyl]acrylic acid 3,5-di-tert-butylphenyl ester, (E)-2-methyl-3-[4-(3-pyridylmethyl-phenyl]acrylic acid 2-methylphenyl ester; the thioester: (E)-2-methyl-3-[4-(3-pyridylmethyl)phenyl]thioacrylic S-acid S-ethyl ester; the alcohol: 4-(3-pyridylmethyl)benzyl alcohol, 4-(3-pyridylhydroxymethyl)phenol, 4-(3-pyridylmethyl)phenol, α-methyl-4-(3-pyridylmethyl)benzyl alcohol; the acids: 4-(3-pyridylmethyl)phenylacetic acid, (E)-3-[4-(3-pyridylmethyl)phenyl]acrylic acid, 3-[4-(3-pyridylmethyl)phenyl]propionic acid, (E)-2-methyl-3-[4-(3-pyridylmethyl)phenyl]acrylic acid, 2-methyl-3-[4-(3-pyridylmethyl)phenyl]propionic acid, (Z)-2-bromo-3-[4-(3-pyridylmethyl)phenyl]acrylic acid, 4-(3-pyridylmethyl)benzoic acid, 2,2-dimethyl-3-[4-(3-pyridylmethyl)phenyl]propionic acid, (E)-2-ethyl-3-[4-(3-pyridylmethyl)phenyl]acrylic acid, (E)-3-[4-(3-pyridylhydroxymethyl)phenyl]acrylic acid, (E)-2-methyl-3-[4-(1-3'-pyridylethyl)phenyl]acrylic acid, (E)-2-methyl-3-[4-(4-methyl-3-pyridylmethyl)phenyl]acrylic acid, (E)-5-(3-pyridylmethyl)-2-(2-carboxyvinyl)thiophene, (E)-5-(3-pyridylmethyl)-2-(2-carboxy-1-propenyl)thiophene, (E)-3-[4-(3-pyridylmethyl)phenyl]-2-butenoic acid, 2-methyl-2-[4-(3-pyridylhydroxymethyl)phenylthio]propionic acid, 2-[4-(3-pyridylmethyl)phenoxy]acetic acid, 2-[4-(3-pyridylmethyl)phenoxy]propionic acid, 2-methyl-2-[4-(3-pyridylmethyl)phenoxy]propionic acid, (E)-2-methyl-3-[3-methyl-4-(3-pyridylmethyl)phenyl]acrylic acid, (E)-3-[3-methyl-4-(3-pyridylmethyl)phenyl]acrylic acid, (E)-2-methyl-3-[3-(3-pyridylmethyl)phenyl]acrylic acid, (E)-2-methyl-3-[3-(4-pyridylmethyl)phenyl]acrylic acid, (E)-2-methyl-3-[4-(4-pyridylmethyl)phenyl]acrylic acid, 2-[4-(3-pyridylmethyl)phenylthio]propionic acid, 2-[4-(3-pyridylmethyl)phenylthio]acetic acid, 2-methyl-2-[4-(3-pyridylmethyl)phenylthio]propionic acid, 3-[4-(3-pyridylhydroxymethyl)phenyl]propionic acid, 2-methyl-3-[4-(1-3'-pyridylethyl)phenyl]propionic acid, 3-[4-(1-3'-pyridylethyl)phenyl]propionic acid, 3-[4-(3-pyridylmethyl)phenyl]butyric acid, 4-[2-(3-pyridylethyl)]benzoic acid, and non-toxic salts and non-toxic acid addition salts thereof.

The following Reference Examples and Examples illustrate the preparation of the pyridine derivatives of the present invention. In the Reference Examples and Examples 'TLC', 'IR', 'NMR' and 'MS' represent respectively 'Thin layer chromatography', 'Infrared absorption spectrum', 'Nuclear magnetic resonance spectrum' and 'Mass spectrum'. Where solvent ratios are specified in chromatographic separations, the ratios are by volume: the solvents in parentheses show the developing solvent used. Except when specified otherwise, infrared spectra are recorded by the liquid film method, and nuclear magnetic resonance spectra are recorded in deuterochloroform ($CDCl_3$) solution.

REFERENCE EXAMPLE 1

4-(3-Pyridylmethyl)benzaldehyde

To a suspension of 3.26 g of 3-chloromethylpyridinyl hydrochloride [prepared as described in J. Amer. Chem. Soc., 73, 4926(1951)] was added dropwise a Grignard reagent [prepared from magnesium (1.07 g), 4-bromobenzaldehyde diethylacetal (11.45 g) and tetrahydrofuran (22 ml)] with cooling in an ice-bath, and the mixture was stirred at room temperature for 2 hours. The reaction mixture was poured into a saturated aqueous solution of ammonium chloride, extracted with diethyl ether, the extract was washed with a saturated aqueous solution of sodium chloride, dried over sodium sulphate and concentrated under reduced pressure. The residue was purified by column chromatography on silica gel using a 1% solution of ethanol in chloroform as eluent to give 2.40 g of 4-(3-pyridylmethyl)benzaldehyde diethylacetal having the following physical characteristics:

TLC(chloroform:methanol=10:1): RF=0.55; IR: $\nu$=2980, 1476, 1420, 1110, 1052, 1024, 713 $cm^{-1}$; NMR: $\delta$=8.4(2H,m), 7.8-6.7(6H,m), 5.4(1H,s), 3.9(2H,s), 3.5(4H,m), 1.2(6H,t); MS: m/e=271, 227, 226, 198, 168, 167, 92.

A mixture of 2.40 g of the acetal compound, obtained above, and 15 ml of 1N hydrochloric acid was stirred at room temperature for one hour. The reaction mixture was diluted with chloroform (40 ml), and neutralized with sodium bicarbonate. The organic layer was washed with water, dried over sodium sulphate and concentrated under reduced pressure. The residue was purified by column chromatography on silica gel using a 1% solution of ethanol in chloroform as eluent to give 1.75 g of the title compound having the following physical characteristics:

TLC(chloroform:methanol=10:1): RF=0.60; IR: $\nu$=3040, 1693, 1608, 1574, 1420, 1213, 1167, 763, 708 cm$^{-1}$; NMR: $\delta$=9.8(1H,s), 8.4(2H,m), 8.0–6.9(6H,m), 4.0(2H,s); MS: m/e=198, 197, 196, 169, 168, 167, 140, 138, 115, 91, 89, 65, 64.

REFERENCE EXAMPLE 2

4-(3-Pyridylmethyl)benzyl chloride hydrochloride

A mixture of 0.27 g of the benzyl alcohol compound [prepared as described in Example 7] and 0.50 ml of thionyl chloride was stirred at 70° to 80° C. for 3 hours, and concentrated under reduced pressure. The residue was purified by recrystallization from ethanol-ethyl acetate to give 0.30 g of the title compound having the following physical characteristics: melting point: 123°–126° C.;

IR(KBr tablet): $\nu$=1632, 1613, 1554, 1515, 1470, 1273, 763, 686, 620 cm$^{-1}$; NMR(DMSO-d$_6$ solution): $\delta$=8.8(1H,broad s), 8.7(1H,d), 8.4(1H,dt), 7.9(1H,dd), 7.3(4H,s), 4.7(2H,s), 4.2(2H,s); MS: m/e=219, 217, 183, 182, 181, 180, 168, 167, 77.

REFERENCE EXAMPLE 3

4-(3-Pyridylmethyl)phenylacetonitrile

A mixture of 0.30 g of the benzyl chloride compound [prepared as described in Reference Example 2], 0.24 g of sodium cyanide and 3 ml of DMSO was stirred at 80° C. to 110° C. for one hour. The reaction mixture was poured into ice-water with 2 ml of 2N aqeous sodium hydroxide, and extracted with diethyl ether. The extract was washed with a saturated aqueous solution of sodium chloride, dried over sodium sulphate and concentrated under reduced pressure. The residue was purified by column chromatography on silica gel using a mixture of cyclohexane and ethyl acetate (1:1) as eluent to give 0.20 g of the title compound having the following physical characteristics:

TLC(cyclohexane:ethyl acetate=1:1): Rf=0.17; IR: $\nu$=2250, 1574, 1510, 1476, 1418, 1027, 790, 713 cm$^{-1}$; NMR: $\delta$=8.5(2H,m), 7.48(1H,dt), 7.4–7.1(5H,m), 3.97(2H,s), 3.70(2H,s); MS: m/e=209, 208, 207, 169, 168, 167, 77.

REFERENCE EXAMPLE 4

4-[(4-Methyl-3-pyridyl)hydroxymethyl]benzaldehyde diethylacetal

Under an atmosphere of nitrogen, a solution of 900 mg of 4-bromobenzaldehyde diethylacetal in 1.8 ml of tetrahydrofuran was added dropwise to 83 mg of magnesium at 50° C. to 60° C., and the mixture was stirred at that temperature for 10 minutes, and then diluted with 2 ml of tetrahydrofuran. The solution, thus obtained, was added dropwise to a solution of 280 mg of 4-methyl-3-formylpyridine [prepared as described in J. Org. Chem., 25, 560(1960)]in 7 ml of tetrahydrofuran at 0° C., and the mixture was stirred at the same temperature for one hour. The reaction mixture was quenched with a saturated aqueous solution of ammonium chloride, and concentrated under reduced pressure. To the residue was added a saturated aqueous solution of sodium bicarbonate, and the mixture was extracted with ethyl acetate. The extract was washed with water, dried over magnesium sulphate and concentrated under reduced pressure. The residue was purified by column chromatography on silica gel using a mixture of ethyl acetate and cyclohexane (7:3) as eluent to give 406 mg of the title compound having the following physical characteristics:

TLC(ethyl acetate): RF=0.57; IR: $\nu$=3300 1610, 1450, 1420, 1380, 1345, 1220, 1060 cm$^{-1}$; NMR: $\delta$=8.48(1H,s), 8.20(1H,d), 7.50–7.10(4H,m), 6.93(1H,d), 5.90(1H,s), 5.40(1H,s), 3.54(4H,q), 2.17(3H,s), 1.20(6H,t); MS: m/e=301, 257, 256, 228, 120, 93, 79.

The following compounds were prepared by the procedure described above.

(a) 4-(3-Pyridylhydroxymethyl)benzaldehyde diethylacetal from 3-formylpyridine and 4-bromobenzaldehyde diethylacetal.

IR: $\nu$=3200, 2990, 1423, 1110, 1052, 712 cm$^{-1}$; NMR: $\delta$=8.3(1H,d), 8.2(1H,dd), 7.7–5.9(6H,m), 5.7(1H,s), 5.4(1H,s), 3.5(4H,m), 1.2(6H,t); MS: m/e=243, 242, 214, 108, 106.

(b) 4-[1-(3-pyridyl)-1-hydroxyethyl]benzaldehyde diethylacetal from 3-acetoxypyridine and 4-bromobenzaldehyde diethylacetal.

TLC(ethyl acetate:cyclohexane=2:1): Rf=0.34; IR: $\nu$=2980, 1580, 1470, 1410, 1370, 1210, 1090, 1050, 920, 810 cm$^{-1}$; NMR: $\delta$=8.6–8.0(2H,m), 7.9–6.8(6H,m), 5.4(1H,s), 4.4–3.2(7H,m), 2.0(3H,s), 1.5–1.0(6H,t); MS: m/e=301, 286, 272, 256, 228.

REFERENCE EXAMPLE 5

4-(4-Methyl-3-pyridylmethyl)benzaldehyde

A mixture of 400 mg of the hydroxymethyl compound (prepared as described in Reference Example 4), 5 ml of benzene and 196 $\mu$of thionyl chloride was stirred at 40° C. for one hour, and concentrated under reduced pressure. To the residue was added a saturated aqueous solution of sodium bicarbonate, and the mixture extracted with chloroform. The extract was washed with water, dried over magnesium sulphate and concentrated under reduced pressure. To the residue were added 5 ml of acetic acid and 175 mg of zinc powder, and the mixture stirred at room temperature for one hour, and then concentrated under reduced pressure. To the residue was added a saturated aqueous solution of sodium bicarbonate, and extracted with ethyl acetate. The extract was washed with water, dried over magnesium sulphate and concentrated under reduced pressure to give 166 mg of the title compound having the following physical characteristics:

TLC(ethyl acetate): Rf=0.50; IR: $\nu$=1700, 1610, 1415, 1220, 1170 cm$^{-1}$; NMR: $\delta$=9.85(1H,s), 8.43–8.17(2H,m), 7.66(1H,s), 7.33–6.67(4H,m), 4.04(2H,s), 2.20(3H,s); MS: m/e=212, 211, 210, 182, 157, 105, 91.

The following compound was prepared by the procedure described above.

(a) 4-[1-(3-pyridylethyl)]benzaldehyde from the product of Reference Example 4(b).

TLC(ethyl acetate:cyclohexane=2:1): Rf=0.53; IR: $\nu$=3400, 3000, 1700, 1610, 1580, 1420, 1220, 1180, 1030, 850 cm$^{-1}$; NMR: $\delta$=9.75(1H,s), 8.5–8.2(2H,m), 7.9–6.8(6H,m), 4.5–3.8(1H,q), 1.8–1.5(3H,d); MS: m/e=211, 196, 182, 168, 167.

REFERENCE EXAMPLE 6

4-(3-Pyridylhydroxymethyl)benzaldehyde

A mixture of 8.55 g of the acetal compound [prepared as described in Reference Example 4(a)], 40 ml of 1N hydrochloric acid and 5 ml of tetrahydrofuran was stirred at room temperature for 2 hours. To the mixture was added a saturated aqueous solution of sodium bicarbonate, and the mixture extracted with chloroform. The extract was washed with water, dried over sodium sulphate and concentrated under reduced pressure to give 6.4 g of the title compound having the following physical characteristics:

melting point: 104°–105° C. (recrystallized from diisopropyl ether-acetone); TLC(chloroform:methanol=10:1): Rf=0.28; IR(KBr tablet): $\nu$=1698, 1605, 1426, 1209, 1071, 820, 776, 717 cm$^{-1}$; NMR: $\delta$=9.96(1H,s), 8.44(1H,d), 8.31(1H,dd), 7.83(2H,d), 7.70(1H,dt), 7.54(2H,d), 7.23(1H,dd); MS: m/e=213, 133, 108, 107, 106.

REFERENCE EXAMPLE 7

3-Methyl-4-(3-pyridylhydroxymethyl)benzaldehyde

To a solution of 1.88 g of 4-bromo-3-methylbenzaldehyde diethylacetal in 20 ml of diethyl ether was added dropwise 5.0 ml of a 1.4M solution of butyllithium in hexane at −70° C. to 0° C., and the mixture was stirred at 0° C. to −50° C. for 50 minutes. To it was added dropwise 0.89 g of 3-formylpyridine at −30° C. to −20° C., and the reaction mixture allowed to warm to room temperature with stirring. After concentration under reduced pressure the residue was stirred with 10 ml of tetrahydrofuran and 10 ml of 2N hydrochloric acid at room temperature for 45 minutes. The reaction mixture was basified with sodium bicarbonate, extracted with diethyl ether, and the extract was washed with a saturated aqueous solution of sodium chloride, dried over sodium sulphate and concentrated under reduced pressure. The residue was purified by column chromatography on silica gel using a mixture of cyclohexane and ethyl acetate (1:2) as eluent to give 1.20 g of the title compound having the following physical characteristics:

melting point: 97.5°–99.0° C. (recrystallized from diisopropyl ether-ethyl acetate); TLC(cyclohexane:ethyl acetate=1:2): Rf=0.12; IR(KBr tablet): $\nu$=3270, 1697, 1604, 1572, 1423, 1025, 847, 798, 712 cm$^{-1}$; NMR: $\delta$=9.8(1H,s), 8.4–8.1(2H,m), 7.7–7.4(4H,m), 7.1(1H,dd), 5.9(1H,s), 2.2(3H,s); MS: m/e=227, 208, 180, 121, 79.

The following compound was prepared by the procedure described above.

(a) 2-Formyl-5-(3-pyridylhydroxymethyl)thiophene from 5-bromo-2-formylthiophene diethylacetal and 3-formylpyridine.

Melting point: 96°–99° C.(recrystallized from diisopropyl ether-acetone); IR(KBr tablet): $\nu$=3080, 2800, 1664, 1457, 1423, 1225, 1216, 1140, 808, 773, 710, 671 cm$^{-1}$; NMR: $\delta$=9.7(1H,s), 8.4(1H,d), 8.3(1H,dd), 7.7(1H,dt), 7.5(1H,d), 7.2(1H,dd), 6.9(1H,d), 6.9(1H,d), 6.0(1H,s); MS: m/e=219, 190, 163, 141, 79.

REFERENCE EXAMPLE 8

2-Formyl-5-(3-pyridylmethyl)thiophene

A mixture of 2.718 g of the thiophene compound [prepared as described in Reference Example 7(a)], 13 ml of pyridine and 1.91 g of acetic anhydride was stirred overnight at room temperature. After concentration under reduced pressure, the residue was treated with a saturated aqueous solution of sodium bicarbonate, and extracted with diethyl ether. The extract was washed with a saturated aqueous solution of sodium chloride, dried over sodium sulphate and concentrated under reduced pressure. The residue was purified by column chromatography on silica gel using a 3% v/v solution of ethanol in chloroform as eluent to give 3.08 g of 2-formyl-5-(3-pyridylacetoxymethyl)thiophene having the following physical characteristics:

TLC(cyclohexane:ethyl acetate=1:2): Rf=0.17; IR: $\nu$=1748, 1674, 1459, 1425, 1373, 1226, 1022, 714 cm$^{-1}$; NMR: $\delta$=9.75(1H,s), 8.6(1H,d), 8.5(1H,dd), 7.7(1H,dd), 7.6(1H,d), 7.25(1H,dd), 7.0(1H,d), 2.2(3H,s).

A mixture of 3.08 g of the compound, obtained above, 15 ml of acetic acid and 1.8 g of zinc powder was stirred at room temperature for 10 minutes. The reaction mixture was filtered and the filtrate was concentrated under reduced pressure. The residue was treated with a saturated aqueous solution of sodium bicarbonate, and extracted with diethyl ether. The extract was washed with a saturated aqueous solution of sodium chloride, dried over sodium sulphate and concentrated under reduced pressure. The residue was purified by column chromatography on silica gel using a mixture of ethyl acetate and cyclohexane (1:1) as eluent to give 0.592 g of the title compound having the following physical characteristics:

melting point: 60°–61° C. (recrystallized from diethyl ether-pentane); TLC(cyclohexane:ethyl acetate=1:2): Rf=0.15; IR(KBr tablet): $\nu$=1650, 1451, 1422, 1234, 820, 760, 720 cm$^{-1}$; NMR: $\delta$=9.7(1H,s), 8.5(2H,m), 7.55(1H,d), 7.5(1H,dt), 7.2(1H,dd), 6.9(1H,d), 4.2(2H,s); MS: m/e=204, 203, 202, 175, 174.

REFERENCE EXAMPLE 9

The following compounds were prepared by the procedure as described in Reference Example 4 and Reference Example 6.

(a) 3-(3-Pyridylhydroxymethyl)benzaldehyde from 3-formylpyridine and 3-bromobenzaldehyde diethylacetal.

Melting point: 113°–115° C. (recrystallized from ethyl acetate-hexane); TLC(ethyl acetate): Rf=0.33; IR(KBr tablet): $\nu$=3130, 1700, 1610, 1485, 1435, 1150, 1070, 720 cm$^{-1}$; NMR: $\delta$=9.82(1H,s), 8.32(1H,d), 8.18(1H,dd), 8.00–6.93(6H,m), 5.83(1H,s), 4.86(1H,broad s); MS: m/e=214, 213, 212, 133, 89.

(b) 3-(4-Pyridylhydroxymethyl)benzaldehyde from 4-formylpyridine and 3-bromobenzaldehyde diethylacetal.

Melting point: 142°–143° C. (recrystallized from ethyl acetate-hexane); TLC(ethyl acetate): Rf=0.44; IR(KBr tablet): $\nu$=3150, 1710, 1610, 1420, 1230, 1140, 1060, 1015, 808 cm$^{-1}$; NMR(CDCl$_3$+DMSO-d$_6$ solution): $\delta$=9.89(1H,s), 8.40(2H,dd), 8.17–7.17(6H,m), 5.80(1H,s), 5.70–4.33(1H,broad s); MS: m/e=213, 135, 107, 106, 79.

(c) 4-(4-Pyridylhydroxymethyl)benzaldehyde from 4-formylpyridine and 4-bromobenzaldehyde diethylacetal.

Melting point: 138°–140° C. (recrystallized from chloroform-cyclohexane); TLC(chloroform:methanol=9:1): Rf=0.35; IR(KBr tablet): $\nu$=1710, 1610, 1430, 1315, 1220, 1070, 1020, 825, 790 cm$^{-1}$; NMR: $\delta$=9.96(1H,s), 8.7–7.0(8H,m), 5.85(1H,s); MS: m/e=213, 184, 167, 166, 107.

REFERENCE EXAMPLE 10

1-Acetyl-4-(3-pyridylmethyl)benzene

A mixture of 547 mg of the α-methylbenzyl alcohol (prepared as described in Example 13), 1.5 g of manganese dioxide and 10 ml of methylene chloride was stirred at room temperature for 3 hours, filtered, and the filtrate was concentrated under reduced pressure to give 407 mg of the title compound having the following physical characteristics:

TLC(ethyl acetate:methylene chloride=2:1): Rf=0.41; IR: $\nu$=1685, 1615, 1280 cm$^{-1}$; NMR: $\delta$=8.42(2H,broad s), 7.80(2H,d), 7.50–6.93(4H,m), 4.00(2H,s), 2.53(3H,s); MS: m/e=211, 196, 167.

REFERENCE EXAMPLE 11

(E)-4-[2-(3-Pyridyl)vinyl]benzoic acid ethyl ester and (Z)-4-[2-(3-pyridyl)-vinyl]benzoic acid ethyl ester A mixture of 16 g of triphenylphosphine, 13.35 g of ethyl 4-bromomethylbenzoate and 50 ml of benzene was stirred at room temperature for 2 days. The precipitate was filtered off, and dried in vacuo to give 20.8 g of (4-ethoxycarbonylbenzyl)triphenylphosphonium bromide.

Melting point: 247°–250° C.; IR(KBr tablet): $\nu$=3420, 2890, 2840, 2770, 1719, 1610, 1438, 1276, 1110, 722, 513 cm$^{-1}$.

A mixture of 2.02 g of the phosphonium compound, thus obtained, 0.432 g of 3-formylpyridine, 5 ml of ethanol and 20 ml of a 0.2N solution of sodium ethoxide in ethanol was stirred at rofom temperature for 30 minutes. The reaction mixture was poured into water, extracted with diethyl ether, and the extract was washed with a saturated aqueous solution of sodium chloride, dried over sodium sulphate and concentrated under reduced pressure. The residue was purified by column chromatography on silica gel using a mixture of cyclohexane and ethyl acetate (2:1) as eluent to give 0.593 g of the (Z)-isomer and 0.351 g of the (E)-isomer. The compounds showed the following characteristics.

(1) The (Z)-isomer:

TLC(cyclohexane:ethyl acetate=1:2): Rf=0.40; IR: $\nu$=1718, 1610, 1369, 1281, 1180, 1107, 1026, 727 cm$^{-1}$; NMR: $\delta$=8.45(2H,m), 7.95(2H,d), 7.48(1H,dt), 7.26(2H,d), 7.12(1H,dd), 6.71(2H,q), 4.36(2H,q), 1.38(3H,t).

(2) The (E)-isomer:

melting point: 105°–106° C. (recrystallized from diisopropyl ether-hexane); TLC(cyclohexane:ethyl acetate=1:2): Rf=0.36; IR(KBr tablet): $\nu$=1700, 1606, 1420, 1365, 1288, 1275, 1180, 1133, 1107, 1022, 978, 763, 707 cm$^{-1}$; NMR: $\delta$=8.74(1H,d), 8.51(1H,dd), 8.05(2H,d), 7.83(1H,dt), 7.36(2H,d), 7.08; (1H,dd), 7.16(2H,s), 4.39(2H,q), 1.40(3H,t).

EXAMPLE 1

(E)-3-[4-(3-Pyridylmethyl)phenyl]acrylic acid methyl ester

A mixture of 200 mg of 4-(3-pyridylmethyl)benzaldehyde (prepared as described in Reference Example 1), 0.14 g of methoxycarbonylmethylenetriphenylphosphorane and 5 ml of chloroform was stirred at room temperature for 3 days, and concentrated under reduced pressure. The residue was purified by column chromatography on silica gel using methylene chloride as eluent to give 48 mg of the title compound having the following physical characteristics:

IR: $\nu$=3030, 1710, 1633, 1570, 1417, 1320, 1169, 1000, 772, 710 cm$^{-1}$; NMR: $\delta$=8.4(2H,m), 7.8–6.9(7H,m), 6.4(1H,d), 3.9(2H,s), 3.7(3H,s); MS: m/e=254, 253, 252, 222, 195, 194, 193, 192, 115, 92.

The following compounds were prepared from the corresponding aldehyde by the procedure described above.

(a) (E)-3-[4-(3-Pyridylmethyl)phenyl]acrylic acid ethyl ester from the aldehyde of Reference Example 1 and ethoxycarbonylmethylenetriphenylphosphorane.

TLC(cyclohexane:ethyl acetate=1:1): Rf=0.23; IR(KBr tablet): $\nu$=1704, 1632, 1605, 1320, 1207, 1176, 1030, 992, 772, 713 cm$^{-1}$; NMR: $\delta$=8.4(2H,m), 7.7–7.0(7H,m), 6.3(1H,d), 4.2(2H,q), 3.9(2H,s), 1.3(3H,t); MS: m/e=268, 267, 238, 223, 222, 195, 194, 193, 192, 191, 167, 115, 92, 65.

(b) (E)-2-Methyl-3-[4-(3-pyridylmethyl)phenyl]acrylic acid ethyl ester from the aldehyde of Reference Example 1 and ethoxycarbonylmethylmethylenetriphenylphosphorane.

TLC(cyclohexane:ethyl acetate=1:1): Rf=0.28; IR: $\nu$=2990, 1707, 1634, 1480, 1422, 1370, 1260, 1208, 1115, 1032, 718 cm$^{-1}$; NMR: $\delta$=8.5(2H,m), 7.69(1H,broad s), 7.6–7.1(6H,m), 4.28(2H,q), 4.00(2H,s), 2.10(3H,d), 1.33(3H,t); MS: m/e=281, 280, 236, 209, 208, 207, 115, 93, 92, 65.

(c) (Z)-2-Bromo-3-[4-(3-pyridylmethyl)phenyl]acrylic acid methyl ester from the aldehyde of Reference Example 1 and methoxycarbonylbromomethylenetriphenylphosphorane.

TLC(cyclohexane:ethyl acetate=1:2): Rf=0.29; IR: $\nu$=1727, 1608, 1432, 1268, 1245, 1207, 1190, 1028, 710 cm$^{-1}$; NMR: $\delta$=8.5(2H,m), 8.22(1H,s), 7.85(2H,d), 7.50(1H,dt), 7.4–7.1(3H,m), 4.01(2H,s), 3.89(3H,s); MS: m/e=333, 331, 253, 252, 193, 192, 115, 92.

(d) (E)-3-[4-(3-Pyridylhydroxymethyl)phenyl]acrylic acid ethyl ester from the aldehyde of Reference Example 6 and ethoxycarbonylmethylenetriphenylphosphorane.

IR(KBr tablet): $\nu$=1709, 1632, 1311, 1203, 1170, 1030, 818, 792 cm$^{-1}$; NMR: $\delta$=8.49(1H,d), 8.35(1H,dd), 7.8–7.1(7H,m), 6.40(1H,d), 5.83(1H,s), 4.25(2H,q), 1.31(3H,t); MS: m/e=283, 254, 238, 177, 131, 108, 107, 106.

(e) (E)-2-Methyl-3-[4-(1-3'-pyridylethyl)phenyl]acrylic acid ethyl ester from the aldehyde of Reference Example 5(a) and ethoxycarbonylmethylmethylenetriphenylphosphorane.

TLC(cyclohexane:ethyl acetate=1:2): Rf=0.59; IR: $\nu$=3000, 1710, 1635, 1425, 1375, 1260, 1115, 1030, 720 cm$^{-1}$; NMR: $\delta$=8.7–8.3(2H,m), 7.8–7.0(7H,m), 4.5–4.0(3H,m), 2.12(3H,s), 1.8–1.5(3H,d), 1.5–1.2(3H,t); MS: m/e=295, 280, 223, 206, 149, 106.

(f) (E)-2-Methyl-3-[4-(4-methyl-3-pyridylmethyl)phenyl]acrylic acid ethyl ester from the aldehyde of Reference Example 5 and ethoxycarbonylmethylmethylenetriphenylphosphorane.

TLC(benzene:ethyl acetate=2:1): Rf=0.52; IR: ν=1710, 1600, 1515, 1450, 1415, 1375, 1265, 1210, 1120 cm$^{-1}$; NMR: δ=8.50-8.20(2H,m), 7.65(1H,s), 7.45-6.90(5H,m), 4.27(2H,q), 4.01(2H,s), 2.45(3H,s), 2.15(3H,d), 1.35(3H,t); MS: m/e=296, 295, 294, 250, 223, 222, 106.

(g) (E)-2-Methyl-3-[3-methyl-4-(3-pyridylhydroxymethyl)phenyl]acrylic acid ethyl ester from the aldehyde of Reference Example 7 and ethoxycarbonylmethylmethylenetriphenylphosphorane.

TLC(cyclohexane:ethyl acetate=1:2): Rf=0.18; IR: ν=3200, 1701, 1632, 1253, 1110, 1028, 757, 715 cm$^{-1}$; NMR: δ=8.3(2H,m), 7.7-7.0(6H,m), 5.9(1H,s), 4.2(2H,q), 2.2(3H,s), 2.1(3H,d), 1.3(3H,t); MS: m/e=312, 311, 266, 239, 233, 205.

(h) (E)-3-[3-Methyl-4-(3-pyridylhydroxymethyl)phenyl]acrylic acid ethyl ester from the aldehyde of Reference Example 7 and ethoxycarbonylmethylenetriphenylphosphorane.

Melting point: 147°-148.5° C.(recrystallized from cyclohexane-ethyl acetate); TLC(cyclohexane:ethyl acetate=1:2): Rf=0.25; IR(KBr tablet): ν=3140, 1712, 1631, 1309, 1294, 1179, 1160, 1032, 993, 802, 723, 659 cm$^{-1}$; NMR: δ=8.3(1H,d), 8.2(1H,dd), 7.7-6.9(6H,m), 6.3(1H,d), 5.9(1H,s), 4.2(2H,q), 2.2(1H,s), 1.3(3H,t); MS: m/e=298, 297, 252.

(i) (E)-2-Methyl-3-[3-(3-pyridylhydroxymethyl)phenyl]acrylic acid ethyl ester from the aldehyde of Reference Example 9(a) and ethoxycarbonylmethylmethylenetriphenylphosphorane.

TLCethyl acetate): Rf=0.55; IR: ν=3180, 1710, 1480, 1430, 1375, 1270, 1120, 1035 cm$^{-1}$; NMR: δ=8.38(1H,d), 8.23(1H,dd), 7.94-6.94(7H,m), 5.77(1H,s), 4.66-3.66(1H,broad s), 4.22(2H,q), 2.00(3H,d), 1.30(3H,t); MS: m/e=298, 297, 296, 253, 252, 225, 224.

(j) (E)-2-Methyl-3-[3-(4-pyridylhydroxymethyl)phenyl]acrylic acid ethyl ester from the aldehyde of Reference Example 9(b) and ethoxycarbonylmethylmethylenetriphenylphosphorane.

Melting point: 101°-102° C.(recrystallized from ethyl acetate-hexane); TLC(ethyl acetate): Rf=0.53; IR(KBr tablet): ν=3130, 1710, 1610, 1420, 1265, 1240, 1120 cm$^{-1}$; NMR: δ=8.27(2H,dd), 7.66-7.46(1H,m), 7.46-7.00(6H,m), 5.70(1H,s), 4.20(2H,q), 4.17-3.50(1H,broad s), 2.00(3H,d), 1.31(3H,t); MS: m/e=297, 225, 224, 145, 117.

(k) (E)-5-(3-Pyridylmethyl)-2-(2-ethoxycarbonylvinyl)thiophene from the aldehyde of Reference Example 8 and ethoxycarbonylmethylenetriphenylphosphorane.

TLC(cyclohexane:ethyl acetate=1:2): Rf=0.26; IR: ν=2990, 1707, 1623, 1460, 1423, 1370, 1312, 1278, 1165, 1040, 806, 717 cm$^{-1}$; NMR: δ=8.5(2H,m), 7.69(1H,d), 7.56(1H,dt), 7.25(1H,dd), 7.08(1H,d), 6.75(1H,d), 6.10(1H,d), 4.23(2H,q), 4.14(2H,s), 1.30(3H,t); MS: m/e=274, 273, 244, 228, 201, 200, 199.

(l) (E)-5-(3-Pyridylmethyl)-2-(2-ethoxycarbonyl-1-propenyl)thiophene from the aldehyde of Reference Example 8 and ethoxycarbonylmethylmethylenetriphenylphosphorane.

TLC(cyclohexane:ethyl acetate=1:2): Rf=0.31; IR: ν=2995, 1698, 1620, 1423, 1366, 1265, 1207, 1108, 1030, 802, 713 cm$^{-1}$; NMR: δ=8.5(2H,m), 7.76(1H,broad s), 7.58(1H,dt), 7.27(1H,dd), 7.12(1H,d), 6.82(1H,d), 4.25(2H,q), 4.18(2H,s), 2.16(3H,d), 1.32(3H,t); MS: m/e=288, 287, 258, 242, 215, 214, 213, 212, 135, 121.

(m) (E)-2-Methyl-3-[4-(4-pyridylhydroxymethyl)phenyl]acrylic acid ethyl ester ester from the aldehyde of Reference Example 9(c) and ethoxycarbonylmethylmethylenetriphenylphosphorane.

Melting point: 154°-156° C.(recrystallized from ethyl acetate-cyclohexane); TLC(chloroform:methanol=9:1): Rf=0.37; IR(KBr tablet): ν=3425, 3100, 3000, 1710, 1635, 1610, 1420, 1375, 1315, 1275, 1215, 1140, 1070, 800, 660 cm$^{-1}$; NMR: δ=8.6-8.1(2H,m), 7.7-7.0(7H,m), 5.75(1H,s), 4.5-3.9(2H,q), 2.06(3H,s), 1.6-1.1(3H,t); MS: m/e=297, 268, 252, 225, 145.

(n) (E)-3-[4-(1-3′-Pyridylethyl)phenyl]acrylic acid ethyl ester from the aldehyde of Reference Example 5(a) and ethoxycarbonylmethylenetriphenylphosphorane.

TLC(ethyl acetate:cyclohexane=2:1): Rf=0.60.

EXAMPLE 2

(E)-2-Ethyl-3-[4-(3-pyridylmethyl)phenyl]acrylic acid ethyl ester

To a suspension of 46 mg of sodium hydride(content 63%) in 3 ml of tetrahydrofuran was added dropwise 0.33 g of diethyl 1-ethoxycarbonylpropylphosphonate at room temperature, and the mixture was stirred at that temperature for 15 minutes. To it was added a solution of 206 mg of the aldehyde (prepared as described in Reference Example 1) in one ml, and the mixture was stirred at room temperature for 1.5 hours. The reaction mixture was acidified with acetic acid, and concentrated under reduced pressure. To the residue was added a saturated aqueous solution of sodium bicarbonate, and extracted with ethyl acetate. The extract was washed with a saturated aqueous solution of sodium chloride, dried over sodium sulphate and concentrated under reduced pressure. The residue was purified by column chromatography on silica gel using a mixture of cyclohexane and ethyl acetate (2:1) as eluent to give 273 mg of the title compound having the following physical characteristics:

TLC(cyclohexane:ethyl acetate=1:2): Rf=0.33; IR: ν=2980, 1707, 1629, 1475, 1421, 1303, 1284, 1237, 1208, 1127, 1048, 1028, 1020, 712 cm$^{-1}$; NMR: δ=8.5(2H,m), 7.66(1H,s), 7.53(1H,dt), 7.5-7.1(5H,m), 4.31(2H,q), 4.02(2H,s), 2.58(2H,q), 1.36(3H,t), 1.18(3H,t); MS: m/e=295, 223, 222, 129, 128, 115, 93, 92, 65.

The following compound was prepared by the procedure described above.

(a) (E)-3-[4-(3-Pyridylmethyl)phenyl]-2-butenoic acid ethyl ester from 1-acetyl-4-(3-pyridylmethyl)benzene (prepared as described in Reference Example 10) and diethyl ethoxycarbonylmethylphosphonate.

TLC(cyclohexane:ethyl acetate=1:2): Rf=0.46; IR: ν=1710, 1630, 1170 cm$^{-1}$; NMR: δ=8.50(2H,m), 7.60-7.02(6H,m), 4.20(2H,q), 4.12(1H,q), 3.98(2H,s), 2.54(3H,d), 1.30(3H,t); MS: m/e=281, 252, 236, 209, 92, 91.

EXAMPLE 3

4-(3-Pyridylmethyl)benzoic acid methyl ester

A mixture of 300 mg of the aldehyde (prepared as described in Reference Example 1), 370 mg of sodium cyanide, 3.0 g of manganese dioxide, 0.18 ml of acetic acid and 15 ml of methanol was stirred overnight at room temperature, filtered through a pad of infusorial earth, and the filtrate was concentrated under reduced pressure. To the residue was added a saturated aqueous solution of sodium bicarbonate, and extracted with chloroform. The extract was washed with water, dried over sodium sulphate and concentrated under reduced pressure. The residue was purified by column chromatography on silica gel using a mixture of cyclohexane and ethyl acetate (3:2) as eluent to give 255 mg of the title compound having the following physical characteristics:

TLC(cyclohexane:ethyl acetate=1:1): Rf=0.23; IR: $\nu$=1720, 1610, 1432, 1282, 1180, 1113, 1022, 760, 719 cm$^{-1}$; NMR: $\delta$=8.5(2H,m), 8.01(2H,d), 7.48(1H,dt), 7.4–7.1(3H,m), 4.03(2H,s), 3.90(3H, s); MS: m/e=227, 196, 169, 168, 167, 166, 141, 140, 139, 115, 92, 89, 65, 63.

EXAMPLE 4

4-(3-Pyridylmethyl)phenylacetic acid hydrochloride

A mixture of 0.14 g of the acetonitrile compound (prepared as described in Reference Example 3) and 2 ml of conc-hydrochloric acid was stirred at 80° to 90° C. for 15 hours, and concentrated under reduced pressure. To the residue was added 2 N aqueous sodium hydroxide, and the solution was concentrated under reduced pressure. These addition-concentration operations were individually repeated using water, dilute hydrochloric acid, and tert-butanol, successively. The residue was dissolved in ethanol, filtered, and the filtrate was concentrated under reduced pressure. The residue was purified by recrystallization from ethanol-diethyl ether to give 0.10 g of the title compound having the following physical characteristics:

Melting point: 151°–154° C.; IR(KBr tablet): $\nu$=1730, 1557, 1462, 1377, 1056, 800, 768, 688, 614 cm$^{-1}$; NMR(D$_2$0 solution): $\delta$=8.74(2H,m) 8.53(1H,dt), 8.07(1H,dd), 7.36(4H,s), 4.47(2H,s), 3.75(2H,s); MS: m/e=227, 184, 183, 182, 181, 180, 168, 167, 152, 128, 115, 104, 103, 91, 89, 78, 77, 65, 63.

EXAMPLE 5

2,2-Dimethyl-3-[4-(3-pyridylmethyl)phenyl]propionic acid ethyl ester

To a 3.0 M solution of lithium diisopropylamide in tetrahydrofuran [prepared from diisopropylamine (0.56 ml), tetrahydrofuran (5 ml) and a 1.4 M solution of butyllithium in hexane (2.2 ml)] was added dropwise 0.41 ml of ethyl isobutyrate at −70° C., and the mixture was stirred at that temperature for 40 minutes. To it was added dropwise a solution of 0.26 g of the benzyl chloride compound (prepared as described in Reference Example 2) in 2.8 ml of a mixture of HMPA and tetrahydrofuran (1:1) at −70° C., and the mixture was stirred at that temperature for 2 hours, and then at room temperature for one hour. The reaction mixture was poured into a saturated aqueous solution of ammonium chloride, and extracted with diethyl ether. The extract was washed with a saturated aqueous solution of sodium chloride, dried over sodium sulphate and concentrated under reduced pressure. The residue was purified by column chromatography on silica gel using a mixture of cyclohexane and ethyl acetate (2:1) as eluent to give 0.27 g of the title compound having the following physical characteristics:

TLC(cyclohexane:ethyl acetate=1:2): Rf=0.37; IR: $\nu$=2980, 1732, 1513, 1478, 1421, 1186, 1127, 1030 cm$^{-1}$; NMR: $\delta$=8.5(2H,m), 7.46(1H,dt), 7.19(1H,dd), 7.06(4H,s), 4.10(2H,q), 3.93(2H,s), 2.82(2H,s), 1.19(3H,t), 1.14(6H,s); MS: m/e=297, 224, 183, 182, 181, 180, 168, 167, 128, 116, 105, 93, 92, 77, 65, 59.

EXAMPLE 6

2-[4-(3-Pyridylhydroxymethyl)phenylthio]propionic acid ethyl ester

A solution of 0.95 g of 4-bromothiophenol in 20 ml of tetrahydrofuran was added dropwise to 7.5 ml of a 1.4 M solution of butyllithium in hexane at −70° to −60° C. After allowed to warm to 0° C., the mixture was stirred at 0° C. for 5 minutes. To it was added a solution of 0.505 g of 3-formylpyridine in 10 ml of tetrahydrofuran at −70° C., and the mixture was stirred at −70° C. for 30 minutes. To the mixture was added 0.91 g of 2-bromopropionic acid ethyl ester at −70° C., and the mixture was stirred at room temperature for one hour. The reaction mixture was poured into a saturated aqueous solution of ammonium chloride, extracted with diethyl ether, and the extract was washed with a saturated aqueous solution of sodium chloride, dried over sodium sulphate and concentrated under reduced pressure. The residue was purified by column chromatography on silica gel using a mixture of cyclohexane and ethyl acetate (1:4) as eluent to give 0.66 g of the title compound having the following physical characteristic:

TLC(cyclohexane:ethyl acetate=1:2): Rf=0.35.

The following compounds were prepared from the corresponding halogen compounds by the procedure described above.

(a) 2-[4-(3-Pyridylhydroxymethyl)phenylthio]acetic acid ethyl ester from iodoacetic acid ethyl ester.

TLC(cyclohexane:ethyl acetate=1:2): Rf=0.16.

(b) 2-Methyl-2-[4-(3-pyridylhydroxymethyl)phenylthio]propionic acid ethyl ester from 2-bromo-2-methylpropionic acid ethyl ester.

TLC(cyclohexane:ethyl acetate=1:2): Rf=0.14.

EXAMPLE 7

4-(3-Pyridylmethyl)benzyl alcohol

A mixture of 0.41 g of the aldehyde (prepared as described in Reference Example 1), 8 ml of ethanol and 78 mg of sodium borohydride was stirred at room temperature for 30 minutes. The reaction mixture was diluted with ethyl acetate, washed with water, and a saturated aqueous solution of sodium chloride, dried over sodium sulphate and concentrated under reduced pressure. The residue was purified by column chromatography on silica gel using a 4% V/V solution of ethanol in chloroform as eluent to give 0.33 g of the title compound having the following physical characteristics:

TLC(chloroform:methanol=10:1): Rf=0.33; IR: $\nu$=3250, 1579, 1510, 1477, 1420, 1046, 1033, 1020, 796, 747, 713 cm$^{-1}$; NMR: $\delta$=8.51(1H,d), 8.47(1H,dd), 7.48(1H,dt), 7.4–7.0(5H,m), 4.64(2H,s), 3.92(2H,s); MS: m/e=200, 199, 198, 180, 170, 169, 168, 167, 115, 107, 93, 92, 91, 89, 79, 77, 65, 63.

EXAMPLE 8

4-(3-Pyridylhydroxymethyl)phenol hydrochloride

A solution of 3.45 g of 4-bromophenol in 50 ml of tetrahydrofuran was added to 35 ml of a 1.3 M solution of butyllithium in hexane below −50° C., and the mixture was allowed to warm to 5°–10° C. for 1.5 hours with stirring. After addition of a solution of 2.15 g of 3-formylpyridine in 20 ml of tetrahydrofuran at −60°

C., the mixture was stirred at room temperature for one hour, and then concentrated under reduced pressure. The residue was dissolved in water, washed with diethyl ether, acidified with 5 ml of conc-hydrochloric acid, washed with diethyl ether, neutralized with sodium bicarbonate, extracted wtih diethyl ether, the extract was dried over sodium sulphate and concentrated under reduced pressure. After addition of 6 N hydrochloric acid to the residue, the solution was concentrated under reduced pressure. The residue was purified by recrystallization from ethanol-diethyl ether to give 1.94 g of the title compound having the following physical characteristics:

melting point: 128°–131° C.; IR(nujol method): $\nu = 3400$, 1660, 1610, 1530, 1507, 1454, 1377, 1254, 1230, 1038, 830, 764, 686 cm$^{-1}$; NMR(D$_2$O solution): $\delta = 8.8$(2H,m), 8.6(1H,d), 8.1(1H,dd), 7.4(2H,d), 7.0(2H,d), 6.1(1H,s).

EXAMPLE 9

4-(3-Pyridylmethyl)phenol hydrochloride

Under an atmosphere of hydrogen, a mixture of 1.9 g of the hydroxymethyl compound (prepared as described in Example 8), 1.0 g of 5% palladium on carbon and 12 ml of acetic acid was stirred at room temperature for 24 hours, and filtered. The filtrate was concentrated under reduced pressure. The residue was dissolved in water, neutralized with sodium bicarbonate, extracted with diethyl ether, and the extract was concentrated under reduced pressure. After addition of 6 N hydrochloric acid to the residue, the solution was concentrated under reduced pressure. The residue was purified by recrystallization from ethanol-diethyl ether to give 0.204 g of the title compound having the following physical characteristics:

melting point: 138°–143° C.; IR(nujol method): $\nu = 3230$, 2630, 1614, 1557, 1513, 1380, 1268, 1220, 846, 817, 795, 775 cm$^{-1}$; NMR(DMS0-d$_6$ solution): $\delta = 8.8$(2H,m), 8.43(1H,d), 7.99(1H,dd), 7.14(2H,d), 6.77(2H,d), 4.10(2H,s); MS: m/e=186, 185, 184, 168, 156.

EXAMPLE 10

4-(3-Pyridylmethyl)phenoxyacetic acid ethyl ester

A mixture of 0.70 g of the phenol compound (prepared as described in Example 9), 0.30 g of sodium hydride (content 63%) and 14 ml of N, N-dimethylformamide was stirred at 100° C. for 20 minutes, and stirred with 0.64 g of ethyl bromoacetate at 70° C. for 2 hours. The reaction mixture was concentrated under reduced pressure, the residue was dissolved in water, and extracted with diethyl ether. The extract was washed with water, and a saturated aqueous solution of sodium chloride, dried over sodium sulphate and concentrated under reduced pressure. The residue was purified by column chromatography on silica gel using a 0.5% V/V solution of ethanol in chloroform as eluent to give 0.166 g of the title compound having the following physical characteristics:

TLC(cyclohexane:ethyl acetate=1:2): Rf=0.23; IR: $\nu = 1761$, 1737, 1612, 1509, 1196, 1083, 1028, 807, 715 cm−1; NMR: $\delta = 8.45$(2H,m), 7.44(1H,dd), 7.3–7.0(3H,m), 6.84(2H,d), 4.59(2H,s), 4.26(2H,1), 3.92(2H,s), 1.28(3H,t); MS: m/e=272, 271, 270, 198, 185.

The following compounds were prepared from the corresponding halogen compounds by the procedure described above.

(a) 2-[4-(3- Pyridylmethyl)phenoxy]propionic acid ethyl ester from ethyl 2-bromopropionate.

TLC(cyclohexane:ethyl acetate=1:2): Rf=0.26; IR: $\nu = 3040$, 2990, 1753, 1732, 1611, 1509, 1245, 1194, 1133, 1096, 1050, 1028, 805, 713 cm$^{-1}$; NMR: $\delta = 8.45$(2h,m), 7.44(1H,dt), 7.18(1H,dd), 7.07(2H,d), 6.81(2H,d), 4.701H,q), 4.20(2H,1), 3.90(2H,s), 1.59(3H,d), 1.23(3H,t); MS: m/e=286, 285, 213, 212, 185.

(b) 2-Methyl-2-[4-(3-pyridylmethyl)phenoxy]propionic acid ethyl ester from ethyl 2-bromo-2-methylpropionate.

TLC(cyclohexane:ethyl acetate=1:2): Rf=0.27; IR: $\nu = 1735$, 1612, 1506, 1287, 1250, 1178, 1141, 1028, 718 cm$^{-1}$; NMR: $\delta = 8.46$(2H,m), 7.45(Lb 1H,d), 7.18(1H,dd), 7.05(2H,d), 6.79(2H,d), 4.22(2H,q), 3.91(2h,s), 1.58(6H,s), 1.24(3H,t); MS: m/e=299, 226, 186, 185, 184.

EXAMPLE 11

(E)-2-Methyl-3-[3-Methyl-4-(3-pyridylmethyl)phenyl]acrylic acid ethyl ester

A mixture of 0.52 g of the hydroxymethyl compound [prepared as described in Example 1(g)] and 2 ml of thionyl chloride was stirred at 60° C. for one hour, and concentrated under reduced pressure. The residue was dissolved in diethyl ether, neutralized with a saturated aqueous solution of sodium bicarbonate, and the organic layer was washed with a saturated aqueous solution of sodium chloride, dried ove sodium sulphate and concentrated under reduced pressure. The residue was stirred with 4 ml of acetic acid and 0.22 g of zinc powder at room temperature for 2 hours, and concentrated under reduced pressure. The residue was dissolved in diethyl ether, neutralized with a saturated aqueous solution of sodium bicarbonate, and extracted with diethyl ether. The extract was washed with a saturated aqueous solution of sodium chloride, dried over sodium sulphate and concentrated under reduced pressure. The residue was purified by column chromatography on silica gel using a mixture of cyclohexane and ethyl acetate (2:1) as eluent to give 0.404 g of the title compound having the following physical characteristics:

TLC(cyclohexane:ethyl acetate=1:2): Rf=0.39; IR: $\nu = 1702$, 1630, 1476, 1420, 1368, 1263, 1232, 1108, 1027, 715 cm$^{-1}$; NMR: $\delta = 8.48$(2H,m), 7.67(1H, broad s), 7.42(1H,dt), 7.33–7.00(4H,m), 4.28(2H,q),3.99(2H,s), 2.27(3H,s), 2.13(3H,d), 1.34(3h,t); Ms: m/e=296, 295, 294, 250, 223, 92.

The following compounds were prepared from the corresponding hydroxymethyl compounds by the procedure described above.

(a) (E)-3-[3-Methyl-4-(3-pyridylmethyl)phenyl]acrylic acid ethyl ester from the product of Example 1(h).

TLC(cyclohexane:ethyl acetate=1:2): Rf=0.35; IR: $\nu = 2970$, 1710, 1634, 1419, 1320, 1173, 1162, 1127, 984, 713 cm$^{-1}$; NMR: $\delta = 8.47$(2H,m), 7.66(1H,d), 7.5–7.0(5h,m), 6.41(1H,d), 4.26(2H,q), 3.99(2H,s), 2.26(3H,s), 1.33(3H,t); MS: m/e=282, 281, 252, 237, 236.

(b) (E)-2-Methyl-3-[3-(3-pyridylmethyl)phenyl]acrylic acid ethyl ester from the product of Example 1(i).

TLC(benzene:ethyl acetate=2:1) : Rf=0.50; IR: $\nu = 1715$, 1483, 1438, 1375, 1270, 1235, 1120 cm$^{-1}$; NMR: $\delta = 8.60$–8.40(2H,m), 7.70–7.60(1H,m), 7.50 1H,dt), 7.40–7.00(5H,m), 4.28(2H,q), 4.01(2H,s), 2.08(3H,d), 1.35(3H,t); MS: m/e=282, 281, 280, 237, 218.

(c) (E)-2-Methyl-3-[3-(4-pyridylmethyl)phenyl]acrylic acid ethyl ester from the product of Example 1(j).

TLC(benzene:ethyl acetate=2:1): Rf=0.45; IR: ν=1705, 1600, 1415, 1370, 1265, 1225, 1110 cm⁻¹; NMR: δ=8.53(2H,dd), 7.67(1H,d), 7.40–7.00(6H,m), 4.27(2H,q), 4.00(2H,s), 2.08(3H,d), 1.35(3h,t); MS: m/e=282, 281, 280, 236, 208.

(d) (E)-2-Methyl-3-[4-(4-pyridylmethyl)phenyl]acrylic acid ethyl ester from the product of Example 1(m).

TLC(cyclohexane:ethyl acetate=2:1): Rf=0.44; IR: ν=3000, 1710, 1600, 1510, 1420, 1370, 1260, 1210, 1125, 1115 cm⁻¹; NMR: δ=8.7–8.3(2H,m), 7.8–6.9(7H,m), 4.5–4.1(2H,q), 4.00(2H,s), 2.10(3H,s), 1.5–1.3(3H,t); MS: m/e=281, 252, 236, 209, 208.

(e) 2-[4-(3-Pyridylmethyl)phenylthio]propionic acid ethyl ester from the product of Example 6.

TLC(cyclohexane:ethyl acetate=1:2): Rf=0.35; IR: ν=2890, 1728, 1573, 1420, 1257, 1177, 1158, 1027, 1018, 781, 712 cm⁻¹; NMR: δ=8.5(2H,m), 7.3–7.0(3H,m), 4.10(2H,q), 3.95(2H,s), 3.74(1H,1), 1.46(3h,d), 1.14(3H,t); MS: m/e=301, 229, 228, 92.

(f) 2-[4-)3-Pyridylmethyl)phenylthio]acetic acid ethyl ester from the product of Example 6(a).

TLC(cyclohexane:ethyl acetate=1:2): Rf=0.28; IR: ν=2990, 1734, 1576, 1492, 1475, 1420, 1272, 1150, 1130, 1028, 710 cm⁻¹; NMR: δ=8.5(2H,m), 7.5–7.0(6H,m), 4.16(2H,q), 3.95(2H,s), 3.60(2H,s), 1.20(3H,t); MS: m/e=288, 287, 215, 214, 201.

(g) 2-Methyl-'2-[4-(3-pyridylmethyl)phenylthio]propionic acid ethyl ester from the product of Example 6(b).

TLC(cyclohexane:ethyl acetate=1:2): Rf=0.27; IR: ν=2990, 1727, 1580, 1480, 1423, 1270, 1154, 1122, 1030, 714 cm⁻¹; NMR: δ=8.5(2H,m), 7.44(1H,m), 7.42(2H,d), 7.2(1H,m), 7.13(2H,d), 4.10(2H,q), 3.98(2H,s), 1.48(6H,s), 1.19(3H,t); MS: m/e=315, 243, 242, 201, 200.

EXAMPLE 12

3-[4-(3-Pyridylmethyl)phenyl]propionic acid ethyl ester

A mixture of 435 mg of the acrylic acid compound [prepared as described in Example 1(a)], 0.2 g of 5% palladium on carbon and 5 ml of ethanol was stirred overnight at room temperature under an atmosphere of hydrogen. The reaction mixture was filtered, and the filtrate was concentrated under reduced pressure. The residue was purified by column chromatography on silica gel using a 0.4% V/V solution of ethanol in chloroform as eluent to give 435 mg of the title compound having the following physical characteristics:

TLC(chloroform:methanol=10:1): Rf=0.61; IR: ν=1736, 1515, 1478, 1420, 1375, 1185, 1031, 717 cm⁻¹; NMR: δ=8.5(2H,m), 7.48(1H,dt), 7.3–7.1(1H,m), 7.12(4H,s), 4.12(2H,q), 3.94(2H,s), 2.9(2H,m), 2.6(2H,m), 1.20(3H,t); MS: m/e=296, 197, 196, 195, 194, 182, 180, 167, 92.

The following compounds were prepared from the corresponding compounds by the procedure described above.

(a) 2-Methyl-3-[4-(3-pyridylmethyl)phenyl]propionic acid ethyl ester from the product of Example 1(b).

TLC(cyclohexane:ethyl acetate=1:1): Rf=0.30; IR: ν=2290, 1734, 1513, 1477, 1420, 1378, 1176, 1028, 715 cm⁻¹; NMR: δ=8.5(2H,m), 7.48 1H,dt), 7.25(1H,dd), 7.12(4H,s), 4.10(2H,q), 3.95(2H,s), 2.1–1.5(3H,m), 1.3–1.1(6H,m); MS: m/e=284, 283, 268, 211, 209, 183, 182, 180, 167, 92, 91.

(b) 3-[4-(3-Pyridylhydroxymethyl)phenyl]propionic acid ethyl ester from the product of Example 1(d).

Melting point: 99°–100° C.(recrystallized from acetone-diisopropyl ether); TLC(chloroform:methanol=10:1): Rf=0.23; IR(KBr tablet): ν=3430, 3150, 1730, 1185, 1167, 1062, 1033, 816, 720 cm⁻¹; NMR: δ=8.47(1H,d), 8.32(1H,dd), 7.69(1H,dt), 7.4–7.0(5H,m), 5.78(1H,s), 4.09(2H,q), 2.91(2H,t), 2.56(2H,t), 1.18(3H,t); MS: m/e=286, 285, 213, 212, 133.

(c) 2-Methyl-3-[4-(1-3'-pyridylethyl)phenyl]propionic acid ethyl ester from the product of Example 1(e).

TLC(cyclohexane:ethyl acetate=1:2): Rf=0.68; IR: ν=3000, 1740, 1580, 1520, 1460, 1430, 1385, 1180, 1030, 720 cm⁻¹; NMR: δ=8.6–8.3(2H,m), 7.7–6.8(6H,m), 4.3–3.8(3H,m), 3.2–2.4(3H,m), 1.8–1.5(3H,d), 1.4–0.9(6H,dt); MS: m/e=297, 282, 224, 208, 196.

(d) 3-[4-(1-3'-Pyridylethyl)phenyl]propionic acid ethyl ester from the product of Example 1(n).

TLC(cyclohexane:ethyl acetate=1:1): Rf=0.55; IR: ν=3000, 1738, 1515, 1420, 1380, 1185, 1160, 1205, 720 cm⁻¹; NMR: δ=8.7–8.3(2H,m), 7.6–7.0(6H,m), 4.3–3.9(3h,m), 3.1–2.4(4H,m), 1.8–1.5(3H,d), 1.4–1.1(;b 3H,t); MS: m/e=283, 268, 211, 210, 194.

(e) 3-[4-(3-Pyridylmethyl)phenyl]butyric acid ethyl ester from the product of Example 2(a).

TLC(cyclohexane:ethyl acetate=1:2): Rf=0.59; IR: ν=3000, 1740, 1425, 1180, 1035, 720 cm⁻¹; NMR: δ=8.6–8.3(2H,m), 7.6–7.0(6H,m), 4.06(2H,q), 3.93(2H,s), 3.26(1H,m), 2.54(2H,dd), 1.28(3H,d), 1.15(3H,t); MS: m/e=283, 269, 254, 238, 210.

(f) 4-[2-(3-pyridylethyl)]benzoic acid ethyl ester from the (Z)-isomer of Reference Example 11.

TLC(cyclohexane:ethyl acetate=1:2): Rf=0.31; IR: ν=1713, 1612, 1423, 1370, 1283, 1180, 1109, 1026, 718 cm⁻¹; NMR: δ=8.45(2H,m), 7.96(2H,d), 7.41(1H,dt), 7.2(3H,m), 4.37(2H,q), 2.97 (4H,s), 1.39(3H,t); MS: m/e=255, 163, 135, 107, 92.

EXAMPLE 13

α-Methyl-4-(3-pyridylmethyl)benzyl alcohol

Under an atmosphere of nitrogen, 1.5 ml of a 3M solution of methylmagnesium iodide in diethyl ether were added to a solution of 830 mg of the aldehyde (prepared as described in Reference Example 1) in 20 ml of tetrahydrofuran at −70° C., the mixture was allowed to warm from −70° C. to room temperature over a period of one hour with stirring, poured into a saturated aqueous solution of amonium chloride, and extracted with diethyl ether. The extract was washed with water, and a saturated aqueous solution of sodium chloride, dried over sodium sulphate and concentrated under reduced pressure. The residue was purified by column chromatography on silica gel using a mixture of cyclohexane and ethyl acetate (1:1) as eluent to give 547 mg of the title compound having the following physical characteristics:

TLC(benzene:ethyl acetate=1:2): Rf=0.27; IR: ν=3400, 2950, 1420, 1090, 710 cm⁻¹; NMR: δ=8.30(2H,broad s), 7.50–6.93(6H,m) 4.80(1H,q), 3.88(2H,s), 2.80 (1H,broad s), 1.45(3H,d); MS: m/e=213, 198, 170, 92.

EXAMPLE 14

(E)-3-[4-(3-Pyridylmethyl)phenyl]acrylic acid hydrochloride

A mixture of 105 mg of the ester compound [prepared as described in Example 1(a)], 0.40 ml of 2 N aqueous sodium hydroxide and 1 ml of ethanol was stirred overnight at room temperature, and concentrated under reduced pressure. The residue was acidified with 1 N hydrochloric acid, and concentrated under reduced pressure. After addition of tert-butanol to the residue, the solution was concentrated under reduced pressure. The residue was dissolved in absolute ethanol, filtered, and the filtrate was concentrated under reduced pressure. The residue was purified by recyrstallization from ethanol-diethyl ether to give 68 mg of the title compound having the following physical characeristics:

melting point: 219°–222° C.; IR (KBr tablet); $\nu=1702$, 1634, 1323, 1226, 1175, 685 cm$^{-1}$; NMR(D$_2$O solution): $\delta=8.88$(2H,m), 8.65(1H,d), 8.18(1H,dd), 7.9–7.4(5H,m), 6.54(1H,d), 4.39(2H,s); MS: m/e=239, 238, 196, 194, 193, 192, 191, 169, 167, 115.

The following compounds were prepared from the corresponding ester compounds by the procedure described above.

(1) 3-[4-(3-Pyridylmethyl)phenyl]propionic acid hydrochloride from the product of Example 12.

Melting point: 114°–117° C.(recrystallized from ethanol-diethyl ether); IR(KBr tablet): $\nu=3160$, 3120, 1720, 1534, 1450, 1405, 1177, 1008, 922, 791, 680 cm$^{-1}$; NMR(D$_2$O solution): $\delta=8.76$(2H,m), 8.53(1H,d), 8.07(1H,dd), 7.31(4H,s), 4.26(2H,s), 3.1–2.6(4H,m); MS: m/e=241, 240, 198, 197, 196, 182, 181, 169, 168, 167, 107, 92.

(2) (E)-2-Methyl-3-[4-(3-pyridylmethyl)pehnyl]acrylic acid hydrochloride from the product of Example 1(b).

Melting point: 178°–180° C. (recrystallized from ethanol-diethyl ether); IR(KBr tablet): $\nu=1690$, 1527, 1450, 1240, 1216, 1123, 851, 800, 522 cm$^{-1}$; NMR(D$_2$O solution): $\delta=8.85$(2H,m), 8.68(1H,d), 8.17(1H,dd), 7.72(1H,broad s), 7.54(4H,s), 4.39(2H,s), 2.10(3H,d); MS: m/e=253, 210, 109, 108, 194, 169, 115, 92.

(3) 2-Methyl-3-[4-(3-pyridylmethyl)phenyl]propionic acid hydrochloride from the product of Example 12(a).

Melting point: 126°–131° C. (recrystallized from ethanol-diethyl ether); IR(KBr tablet): $\nu=1720$, 1630, 1553, 1466, 1180, 684 cm$^{-1}$; NMR(D$_2$O solution ): $\delta=8.9$(2H,m), 8.55(1H,d), 8.10(1H,dd), 7.32(4H,s), 4.29 (2h,s), 2.86(3H,m), 1.2(3H,m); MS: m/e=240, 212, 211, 210, 196, 183, 182, 181, 180, 167, 92, 91.

(4) (2)-2-Bromo-3-[4-(3-pyuridylemthyl)phenyl]acrylic acid hydrochloride from the product of Example1(c).

Melting point: 192°–196° C. (recrystallized from ethanol-diethyl ether); IR(KBr tablet): $\nu=1700$, 1607, 1531, 1380, 1214, 808, 681 cm$^{-1}$; NMR(D$_2$O solution): $\delta=9.0$(2H,m), 8.65(1H,d), 8.27(1H,dd), 8.17(1H,s), 7.88 (2H,d), 7.49(2H,d), 4.44(2H,s); MS: m/e=319, 317, 274, 272, 195, 194, 193, 192, 191, 167, 165, 139, 115, 89, 65, 63.

(5) 4-(3-Pyridylmethyl)benzoic acid hydrochloride from the product of Example 3.

Melting point: 211°–213° C.(recrystallized from ethanol-diethyl ether); IR(KBr tablet): $\nu=3020$, 1714, 1613, 1557, 1428, 1322, 1295, 780, 759, 688 cm$^{-1}$; NMR(D$_2$O solution): $\delta=8.9$(2H,m), 8.69(1H,dt), 8.23(1H,dd), 8.04(2H,d), 7.54(2H,d), 4.45(2lH,s); MS: m/e=214, 213, 212, 169, 168, 167, 166, 139, 115.

(6) 2,2-Dimethyl-3-[4-(3-pyridylmethyl)phenyl]propionic acid hydrochloride from the product of Example 5.

Melting point: 147°–150° C.(recrystallized from ethanol-diethyl ether); IR(KBr tablet): $\nu=3400$, 2980, 1710, 1628, 1549, 1465, 1180, 1121, 678 cm$^{-1}$; NMR(D$_2$O+DMSO solution): $\delta=8.76$(2lH,m), 8.54(1H,d), 8.06(1H,dd), 7.29(4H,s), 4.26(2H,s), 2.87(2H,s), 1.18(6H,s); MS: m/e=225, 223, 183, 182, 180, 167, 55.

(b 7) (E)-2-Ethyl-3-[4-(3-pyridylmethyl)phenyl]acrylic acid hydrochloride from the product of Example 2.

Melting point: 153°–163° C.(recrystallized from ethanol-diethyl ether); IR(KBr tablet: $\nu=3040$, 2960, 2810, 1700, 1623, 1614, 1553, 1390, 1181, 1128, 780, 684, 610 cm$^{-1}$; NMR(DMSO-d$_6$ solution): $\delta=9.01$(1lH,broad · s), 8.89(1H,d), 8.57(1H,d), 8.09(1H,dd), 7.59(1H,s), 7.47(4H,s), 4.31(2H,s), 2.5(2H,m), 1.10(3H,t); MS: m/e=267, 224, 223, 222, 209, 208, 195, 194, 167, 129, 128, 115, 93, 92, 65.

(8)(E)-3-[4-(3-Pyridylhydroxymethyl)phenyl]acrylic acid hydrochloride from the product of Example 1(d).

Melting point: 161°–173° C.(recrystallized from ethanol-diethyl ether); IR(KBr tablet): $\nu=1690$, 1630, 1318, 1286, 812, 683 cm$^{-1}$; NMR(D$_2$O solution): $\delta=9.12$(1H,m), 9.01(1lH,d), 8.79(1H,broad s), 8.30(1H,dd), 7.70(1H,d), 7.67(4H,s), 6.52(1H,d), 6.38(1H,s); MS: m/e=255, 211, 210, 132, 79.

(9) (E)-2-Methyl-3-[4-(1-3'-pyridylethyl)phenyl]acrylic acid hydrochloride from the product of Example 1(e).

IR(KBr tablet): $\nu=1700$, 1535, 1455, 1405, 1380, 1250, 1225, 1130, 830, 690 cm−1; NMR(D$_2$O solution): $\delta=8.8$–8.5(2lH,m), 8.5–7.6(2H,m), 7.5–6.9(5H,m), 4.6–4.2(1H,m); MS: m/e=267, 252, 223, 208, 206.

(10) (E)-2-Methyl-3-[4-(4-methyl-3-pyridylmethyl)phenyl]acrylic acid hydrochloride from the product of Example 1(f).

Melting point: 218°–221° C.(recrystallized from water); IR(KBr tablet): $\nu=1675$, 1438, 1330, 1300 cm$^{-1}$; NMR(D$_2$0 solution): $\delta=8.75$(1H,d), 8.65(1H,s), 8.04(1H,d), 7.70–7.50(1H,m), 7.39(4H,s), 4.36(2H,s), 2.66(3H,s), 2.05(3H,d); MS: m/e=267, 224, 223, 222, 208.

(11) (E)-5-(3-Pyridylmethyl)-2-(2-carboxyvinyl)thiophene hydrochloride from the product of Example 1(k).

Melting point: 169°–173° C.(recrystallized from ethanol-diethyl ether); IR(KBr tablet): $\nu=3050$, 3000, 1690, 1618, 1529, 1227, 1196, 1177, 956 cm−1; NMR(DMSO-d$_6$ solution): $\delta=8.93$(1H,broad s), 8.85(1H,d), 8.54(1H,dt), 8.06(1H,dd), 7.68(1H,d), 7.39(1H,d), 7.07(1H,d), 6.10(1H,d), 4.48(2H,s); MS: m/e=245, 202, 201, 200, 199.

(12) (E)-5-(3-Pyridylmethyl)-2-(2-carboxy-1-propenyl(thiophene hydrochloride from the product of Example 1(l).

Melting point: 186°–191° C.(recrystallized from ethanol-diethyl ether); IR(KBr tablet): $\nu=2710$, 1680, 1612, 1365, 1248, 1197, 1110, 808, 685 cm$^{-1}$; NMR(DMSO-d$_6$ solution): $\delta=8.99$(1H,d), 8.88(1H,d), 8.55(1H,dd), 8.06(1H,dd), 7.75(1H,broad s), 7.37(1H,d), 7.14(1H,d), 4.52(2H,s), 2.06(3H,d); MS: m/e=259, 217, 216, 215, 200.

(13) (E)-3-[4-(3-Pyridylmethyl)phenyl]-2-butenoic acid hydrochloride from the product of Example 2(a).

Melting point: 162°–167° C.(recrystallized from ethanol); IR(KBr tablet): $\nu=1705$, 1175 cm$^{-1}$; NMR(DMSO-d$_6$ solution): $\delta=9.0$–8.7(2H,m), 8.5–8.3(1H,m), 8.06–7.8(1H,m), 7.7–7.2(4H,m), 6.12(1H,s), 4.22(2H,s), 2.47(3H,s); MS: m/e=253, 209, 194, 169, 115.

(14) 2-Methyl-2-[4-(3-pyridylhydroxymethyl)phenylthio]propionic acid hydrochloride from the product of Example 6(b).

IR(KBr tablet): $\nu=3400$, 1706, 1630, 1463, 1270, 1157, 1122, 790 cm$^{-1}$; NMR(DMSO-d$_6$ solution): $\delta=8.95$(1H,broad s), 8.83(1H,d), 8.53(1H,d), 8.02(1H,dd), 7.48(4H,s), 6.08(1H,s), 1.39(6H,s); MS: m/e=259, 258, 226, 217, 185.

(15) 2-[4-(3-Pyridylmethyl)phenoxy]acetic acid hydrochloride from the product of Example 10.

Melting point: 138°–141° C.(recrystallized from ethanol-diethyl ether); IR(KBr tablet): $\nu=3420$, 2980, 1756, 1548, 1512, 1185, 1081, 822, 692, 613 cm$^{-1}$; NMR(DMSO-d$_6$ solution): $\delta=8.90$(1H,broad s), 8.80(1H,d), 8.48(1H,d), 8.00(1H,dd), 7.27(2H,d), 6.88(2H,d), 4.66(2H,s), 4.16(2H,s); MS: m/e=243, 199, 198, 184, 170.

(16) 2-[4-(3Pyridylmethyl)phenoxy]propionic acid hydrochloride from the product of Example 10(a).

IR(nujol method): $\nu=1738$, 1610, 1510, 1467, 1378, 1245, 1183, 1135, 1100, 810, 690 cm$^{-1}$; NMR(D$_2$O solution): $\delta=8.7$(2H,m), 8.48(1H,dt), 8.03(1H,dd), 7.30(2H,d), 6.99(2H,d), 4.94(1H,q), 4.21(2H,s), 1.66(3H,d); MS: m/e=257, 213, 212, 199, 198.

(17) 2-Methyl-2-[4-(3-pyridylmethyl)phenoxy]propionic acid hydrochloride from the product of Example 10(b).

IR(KBr tablet): $\nu=3400$, 1728, 1607, 1550, 1504, 1466, 1238, 1145, 970, 804, 680 cm$^{-1}$; NMR(DMSO-d$_6$ solution): $\delta=8.7$(2H,m), 8.14(1H,d), 7.74(1H,m), 7.21(2H,d), 6.80(2H,d), 4.06(2H,s), 1.50(6H,s); MS: m/e=271, 227, 226, 212, 185.

(18) (E)-2-Methyl-3-[3-methyl-4-(3-pyridylmethyl)phenyl]acrylic acid hydrochloride from the product of Example 11.

Melting point: 153°–157° C.(recrystallized from ethanol-diethyl ether); IR(KBr tablet): $\nu=3420$, 3050, 2760, 2710, 1690, 1630, 1550, 1394, 1370, 1210, 1120, 833, 690 cm$^{-1}$; NMR(D$_2$O solution): $\delta=8.99$(1H,d), 8.89(1H,broad s), 8.55(1H,d), 8.23(1H,d), 7.6–7.1(4H,m), 4.43(2H,s), 2.37(3H,s), 2.02(3H,d); MS: m/e=267, 224, 223, 222, 208.

(19) (E)-3-[3-Methyl-4-(3-pyridylmethyl)phenyl]acrylic acid hydrochloride from the product of Example 11(a).

Melting point: 167°–171° C.(recrystallized from ethanol-diethyl ether); IR(KBr tablet): $\nu=1697$, 1628, 1550, 1370, 1268, 1198, 1180, 978, 812, 683 cm$^{-1}$; NMR(D$_2$O solution): $\delta=8.91$(1H,d), 8.79(1H,broad s), 8.50(1H,t), 8.17(1H,dd), 7.46(1H,d), 7.32(3H,m), 6.30(1H,d), 4.35(2H,s), 2.32(3H,s); MS: m/e=263, 210, 209, 208, 183.

(20) (E)-2-Methyl-3-[3-(3-pyridylmethyl)phenyl]acrylic acid hydrochloride from the product of Example 11(b).

IR(KBr tablet): $\nu=1700$, 1635, 1550, 1375, 1210, 1120 cm$^{-1}$; NMR(D$_2$O solution): $\delta=9.20$–8.80(2H,m), 8.62(1H,d), 8.23(1H,dd), 7.70–7.10(5H,m), 4.43(2H,s), 2.05(3H,d); Ms: m/e=253, 209, 208, 194, 169.

(21) (E)-2-Methyl-3-[3-(4-pyridylmethyl)phenyl]acrylic acid hydrochloride from the product of Example 11(c).

Melting point: 196°–200° C.(recrystallized from ethanol-diethyl ether); IR(KBr tablet): $\nu=1700$, 1640, 1605, 1510, 1385, 1230, 1125, 800 cm$^{-1}$; NMR(D$_2$O solution): $\delta=8.90$(2H,d), 8.07(2H,d), 7.70–7.00(5H,m), 4.46(2H,s), 2.03(3H,d); MS: m/e=253, 210, 209, 208, 195.

(22) (E)-2-Methyl-3-[4-(4-pyridylmethyl)phenyl]acrylic acid hydrochloride from the product of Example 11(d).

Melting point: 211°–213° C.(not recrystallized); IR(KBr tablet): $\nu=1700$, 1640, 1610, 1500, 1385, 200, 1190, 1120, 825, 780 cm$^{-1}$; NMR(methanol-d$_4$ solution): $\delta=8.9$–8.6(2H,m), 8.2–7.8(2H,m), 7.8–7.2(5H,m), 4.4(2H,s), 2.06(3H,s); MS: m/e=253, 209, 208, 194, 169.

(23) 2-[4-(3-Pyridylmethyl)phenylthio]propionic acid hydrochloride from the product of Example 11(e).

IR(KBr tablet): $\nu=3400$, 1725, 1627, 1607, 1550, 1170, 781, 682 cm$^{-1}$; NMR(DMSO-d$_6$ solution): $\delta=8.85$(1H,broad s), 8.75(1H,d), 8.34(1H,d), 7.90(1H,dd), 7.37(4H,m), 4.19(2H,s), 3.91(1H,q), 1.37(3H,d); MS: m/e=229, 228, 214, 196, 169.

(24) 2-[4-(3-Pyridylmethyl)phenylthio]acetic acid hydrochloride from the product of Example 11(f).

Melting point: 133°–136° C.(recrystallized from ethanol-diethyl ether); IR(KBr tablet): $\nu=3400$, 3000, 2930, 2870, 1728, 1630, 1623, 1547, 1146, 797, 785, 685, 487 cm$^{-1}$; NMR(DMSO-d$_6$ solution): $\delta=8.90$(1H,broad s), 8.44(1H,dt), 7.97(1H,dd), 7.31(4H,s), 4.18(2H,s), 3.78(2H,s); MS: m/e=216, 215, 214, 201, 200.

(25) 2-Methyl-2-[4-(3-pyridylmethyl)phenylthio]propionic acid hydrochloride from the product of Example 11(g).

IR(KBr tablet): $\nu=3400$, 1714, 1550, 1463, 1216, 1150, 1124, 810, 785, 687 cm$^{-1}$; NMR(DMSO-d$_6$ solution):$\delta=8.93$(1H,broad s), 8.80(1H,d), 8.45(1H,d), 7.99(1 H,dd), 7.39(4H,m), 4.25(2H,s), 1.37(6H,s); MS: m/e=243, 242, 228, 210, 169.

(26) 3-[4-(3-Pyridylhydroxymethyl)phenyl]propionic acid hydrochloride from the product of Example 12(b).

IR: $\nu=1720$, 1550, 1464, 1450, 1400, 1190, 1044, 815 cm$^{-1}$; NMR(D$_2$O solution): $\delta=8.90$(1H,broad s), 8.79(1H,d), 8.61(1H,d), 7.5–7.3(5H,m), 6.18(1H,s), 3.1–2.6(4H,m); MS: m/e=257, 256, 214, 213, 212.

(27) 2-Methyl-3-[4-(1-3'-pyridylethyl)phenyl]propionic acid hydrochloride from the product of Example 11(c).

IR: $\nu=1720$, 1630, 1550, 1510, 1460, 1380, 1270, 1225, 1190, 820, 690cm$^{-1}$; NMR(D$_2$O solution): $\delta=8.9$–8.4(3H,m), 8.2–7.8(1H,m), 7.27(4H,s), 4.9–4.3(2H,m), 3.1–2.6(3H,m), 1.9–1.6(3H,d), 1.4–1.0(3H,m); MS: m/e=270, 269, 268, 254, 225.

(28) 3-[4-(1-3'-Pyridylethyl)phenyl]propionic acid hydrochloride from the product of Example 12(d).

IR: $\nu=1720$, 1620, 1380, 1190, 1160, 690 cm$^{-1}$; NMR(D$_2$O solution): $\delta=8.8$–8.4(3H,m), 8.2–7.8(1H,m), 7.3(4H,s), 4.9–4.3(2H,m), 3.2 –2.5(4H,m), 1.9–1.6(3H,d); MS: m/e=255, 254, 240, 211, 194.

(29) 3-[4-(3-Pyridylmethyl)phenyl]butyric acid hydrochloride from the product of Example 12(e).

Melting point: 167°–168° C.(recrystallized from ethanol); IR(KBr tablet): $\nu=3000$, 1730, 1550, 1165, 690, 620 cm$^{-1}$; NMR(D$_2$O solution): $\delta=8.42$(2H,m), 8.0(2H, m), 7.25(4H,s), 4.21(2H,s), 3.21(1H,m), 2.63(2H,d), 1.24(3H,d); MS: m/e=255, 211, 196, 92.

(30) 4-[2-(3-Pyridylethyl)]benzoic acid hydrochloride from the product of Example 12(f).

Melting point: 234°–240° C. (decomposition, recrystallized from ethanoldiethyl ether); IR(KBr tablet): $\nu$=3430, 3080, 2870, 1689, 1612, 1528, 1384, 1248, 1180, 830, 681 cm$^{-1}$; NMR(DMSO-d$_6$ solution): $\delta$=8.87(1H,broad s), 8.81(1H,d), 8.52(1H,d), 8.02(1H,dd), 7.88(2H,d), 7.39(2H,d), 3.14(4H,m); MS: m/e=227, 184, 183, 136, 135.

EXAMPLE 15

(E)-2-Methyl-3-[4-(3-pyridylmethyl)phenyl]acrylic acid

A mixture of 5.4 g of the ester compound[prepared as described in Example 1(b)], 13 ml of 2N aqueous sodium hydroxide and 40 ml of ethanol was stirred at 30° to 40° C. for 4 hours, and concentrated under reduced pressure. The residue was dissolved in water, washed with diethyl ether, and neutralized with 1 N hydrochloric acid. The precipitate was filtered of, washed with chloroform, and water, and dried in vacuo to give 3.98 g of the title compound having the following physical characteristics:

melting point: 164°–166° C.(not recrystallized); IR(KBr tablet): $\nu$=3400, 1700, 1640, 1580, 1510, 1420, 1340, 1280, 1120, 1050, 990, 860, 790, 710, 650 cm$^{-1}$; NMR(methanol-d$_4$ solution): $\delta$=8.6–8.2(2H,m), 7.9–7.0(7H,m), 4.75(1H,s), 4.04(2H,s), 2.05(3H,s); MS: m/e=253, 209, 194, 169, 92.

EXAMPLE 16

(E)-2-Methyl-3-[4-(3-pyridylmethyl)phenyl]acrylic acid decyl ester

A solution of 126.5 mg of the acrylic acid(prepared as described in Example 15) in 3 ml of methanol was stirred with 0.1 ml of a 10% W/W solution of tetramethylammonium hydroxide in methanol at room temperature for 20 minutes, and the mixture was concentrated under reduced pressure. The residue was dissolved in 3 ml of N,N-dimethylformamide, the solution was stirred overnight with 0.1033 ml of decyl bromide at room temperature, and concentrated under reduced pressure. The residue was purified by column chromatography on silica gel using a 1% V/V solution of ethanol in chloroform as eluent to give 53 mg of the title compound having the following physical characteristics:

IR: $\nu$=2950, 1710, 1635, 1510, 1425, 1260, 1120, 720 cm$^{-1}$; NMR: $\delta$=8.6–8.3(2H,m), 7.8–7.0(7H,m), 4.4–4.1(2H,t), 4.0(2H,s), 2.1(3H,s); MS: m/e=393, 365, 351, 336, 209.

The following compounds were prepared from the corresponding halogen compounds by the procedure described above.

(a) (E)-2-Methyl-3-[4-(3-pyridylmethyl)phenyl]acrylic acid benzyl ester from benzyl chloride.

IR: $\nu$=3050, 1710, 1260, 1220, 1120, 760 cm$^{-1}$; NMR: $\delta$=8.6–8.35(2H,m), 7.8–7.0(12H,m), 5.26(2H,s), 4.0(2H,s), 2.14(3H,s); MS: m/e=343, 298, 233, 209, 92.

(b) (E)-2-Methyl-3-[4-(3-pyridylmethyl)phenyl]acrylic acid biphenylmethyl ester from biphenylmethyl bromide.

IR: $\nu$=3050, 1710, 1500, 1455, 1255, 1210, 1120, 750, 710 cm$^{-1}$; NMR: $\delta$=8.6–8.3(2H,m), 8.2–6.9(18H,m), 4.0(2H,s), 2.18(3H,s); MS: m/e=419, 375, 237, 236, 167.

(c) (E)-2-Methyl-3-[4-(3-pyridylmethyl)phenyl]acrylic acid butyl ester from butyl bromide.

IR: $\nu$=2970, 1710, 1640, 1260, 1120 cm$^{-1}$; NMR: $\delta$=8.6–8.4(2H,m), 7.8–7.0(7H,m), 4.4–4.1(2H,t), 4.0(2H,s), 2.1(3H,s); MS: m/e=309, 252, 238, 223, 92.

EXAMPLE 17

(E)-2-Methyl-3-[4-(3-pyridylmethyl)phenyl]acrylic acid phenyl ester

A solution of 105 mg of pivaloyl chloride in one ml of methylene chloride was added to a solution of 200 mg of the acrylic acid(prepared as described in Example 15) and 0.1257 ml of triethylamine in 5 ml of methylene chloride at room temperature, and the mixture was stirred at room temperature for one hour. To it were added 1.47 g of phenol and 1.323 ml of pyridine, the mixture was stirred overnight at room temperature, and concentrated under reduced pressure. The residue was dissolved in diethyl ether, washed with a saturated aqueous solution of sodium bicarbonate, and a saturated aqueous solution of sodium chloride, dried over sodium sulphate and concentrated under reduced pressure. The residue was purified by column chromatography on silica gel using a mixture of cyclohexane and ethyl acetate (3:2) as eluent to give 158 mg of the title compound having the following physical characteristics:

melting point: 52°–53° C.(recrystallized from diethyl ether-cyclohexane); IR(KBr tablet): $\nu$=1730, 1635, 1480, 1257, 1200, 1090 cm$^{-1}$; NMR: $\delta$=8.7–8.3(2H,m), 8.0–7.0(12H,m), 4.02(2H,s), 2.23(3H,s); MS: m/e=329, 236, 208, 92.

The following compounds were prepared from the corresponding alcohols by the procedure described above.

(a) (E)-2-Methyl-3-[4-(3-pyridylmethyl)phenyl]acrylic acid 3-trifluoromethylphenyl ester from 3-trifluoromethylphenol.

IR: $\nu$=3050, 2950, 1730, 1635, 1450, 1330, 1240, 1200, 1130, 1085 cm$^{-1}$; NMR: $\delta$=8.7–8.3(2H,m), 8.0–7.8(1H,broad s), 7.7–7.0(10H,m), 4.02(2H,s), 2.25(3H,s); MS: m/e=397, 378, 236, 208, 149.

(b) (E)-2-Methyl-3-[4-(3-pyridylmethyl)phenyl]acrylic acid 3,5-di-tert-butylphenyl ester from 3,5-di-tert-butylphenol.

IR: $\nu$=2950, 1730, 1610, 1590, 1480, 1420, 1240, 1200, 1090 cm$^{-1}$; NMR: $\delta$=8.6–8.4(2H,m), 8.0–7.8(1H,m), 7.6–6.9(9H,m), 4.01(2H,s), 2.25(3H,s), 1.3(18H,s); MS: m/e=443, 255, 236, 191, 92.

(c) (E)-2-Methyl-3-[4-(3-pyridylmethyl)phenyl]acrylic acid 2-methylphenyl ester from 2-methylphenol.

IR: $\nu$=3050, 2950, 1730, 1635, 1490, 1425, 1230, 1190, 1120, 1095 cm$^{-1}$; NMR: $\delta$=8.7–8.3(2H,m), 8.0–6.9(11H,m), 4.02(2H,s), 2.25(6H,s); MS: m/e=343, 236, 208, 92.

EXAMPLE 18

(E)-2-Methyl-3-[4-(3-pyridylmethyl)phenyl]thioacrylic S-acid S-ethyl ester hydrochloride To a solution of 253 mg of the acrylic acid(prepared as described in Example 15) in 3 ml of N,N-dimethylformamide were added 326 mg of diethyl phosphorocyanidate(DEPC), 88.57 $\mu$l of ethanethiol and 0.2438 ml of triethylamine, successively, with cooling in an ice-bath, and the mixture was stirred at room temperature for 3 hours. The reaction mixture was diluted with benzene, washed with 5% W/W aqueous citric acid, and a saturated aqueous solution of sodium bicarbonate, dried over sodium sulphate and concentrated under reduced pressure. To the residue was added 1 N hydrochloric acid, and the mixture was concentrated under reduced pressure to give 164 mg of the title compound having the following physical characteristics:

melting point: 132°–135° C. (not recrystallized; IR(KBr tablet): $\nu=1640$, 1548, 1180, 1030, 920, 900, 780, 690, cm$^{-1}$; $\delta=9.0-8.6$(2H,m), 8.4–8.1(1H,m), 8.1–7.8(1H,m), 7.8–7.0(5H,m), 4.28 (2H,s), 3.2–2.8(2H,q), 2.16(3H,s), 1.5–1.1(3H,t); MS: m/e=297, 269, 236, 208, 92.

EXAMPLE 19

(E)-2-Methyl-3-[4-(3-pyridylmethyl)phenyl]acrylic acid mesylate

A mixture of 96 mg of the acrylic acid(prepared as described in Example 15), 24.6 μl of methanesulphonic acid and one ml of water was concentrated under reduced pressure. The residue was dried in vacuo to give 97 mg of the title compound having the following physical characteristics:

melting point: 130°–155° C.(not recrystallized); IR(KBr tablet): $\nu=1700$, 1570, 1460, 1400, 1380, 1220, 1200, 1065, 860, 790, 690 cm$^{-1}$; NMR(D$_2$O solution): $\delta=9.0-8.4$(3H,m), 8.4–8.0(1H,m), 7.7–7.3(5H,m), 4.97 (2H,s), 4.4(2H,s), 3.02(3H,s), 2.05(3H,s); MS: m/e=253, 209, 194, 169, 96.

EXAMPLE 20

(E)-2-Methyl-3-[4-(3-pyridylmethyl)phenyl]acrylic acid solution salt

A solution of 253 mg of the acrylic acid(prepared as described in Example 15) in one ml of 1 N aqueous sodium hydroxide was concentrated under reduced pressure. The residue was purified by recrystallization from ethanol-water-tert-butanol to give 171 mg of the title compound having the following physical characteristics:

melting point: above 200° C.; IR(KBr tablet): $\nu=1555$, 1395, 720 cm$^{-1}$; NMR(D$_2$O solution): $\delta=8.4-8.0$(2H,m), 7.5–6.5(7H,m), 3.70(2H,s), 1.97(3H,s); MS: m/e=209, 149, 148, 124, 91.

The present invention includes within its scope pharmaceutical compositions which comprise at least one new therapeutically useful compound of general formula I, or non-toxic acid addition salt or non-toxic salt thereof, together with a pharmaceutical carrier or coating. In clinical practice, the new compounds of the present invention will normally be administered orally, rectally or parenterally.

Solid compositions for oral administration include compressed tablets, pills, dispersible powders and granules. In such solid compositions one or more of the active compounds is, or are, admixed with at least one inert diluent such as calcium carbonate, potato starch, dextrin, alginic acid, lactose, mannitol, glucose or cacao butter. The compositions may also comprise, as is normal practice, additional substances other than inert diluents, e.g. lubricating agents such as magnesium stearate. The tablets or pills may, if desired, be coated and made into sugar-coated, gelatin-coated, enteric-coated or film-coated tablets or pills, or tablets or pills coated with two or more layers.

Liquid compositions for oral administration include pharmaceutically-acceptable emulsions, solutions, suspensions, syrups and elixirs containing inert diluents commonly used in the art, such as water or liquid paraffin. Besides inert diluents such compositions may also comprise adjuvants such as wetting and suspending agents, and sweetening, flavouring, perfuming and preserving agents.

The compositions according to the invention for oral administration, also include capsules of absorbable material such as gelatin containing one or more of the active substances with or without the addition of diluents or excipients.

Solid compositions for intrarectal administration include suppositories formulated in manner known per se and containing one or more of the active substances.

Preparations according to the invention for parenteral administration include sterile aqueous or non-aqueous solutions, suspensions or emulsions. Examples of non-aqueous solvents or suspending media are propylene glycol, polyethylene glycol, ethanol, vegetable oils such as olive oil, and injectable organic esters such as ethyl oleate and sorbitan esters. These compositions may also include adjuvants such as preserving, wetting, emulsifying and dispersing agents. They may be sterilised, for example by filtration through a bacteria-retaining filter, by incorporation of sterilising agents in the compositions or by irradiation. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance.

The dosage employed depends upon the desired therapeutic effect, the poute of administration, the duration of the treatment, and the age and body weight of the patient.

In the adult, each dose per person is generally between 0.1 mg and 1 g by oral, intrarectal, intravenous, intramuscular or subcutaneous administration in the treatment or prevention of inflammation, hypertension, thrombus, cerebral apoplexy, asthma, myocardial infarction, cardistenosis, cerebral infarction and acute cardiac death. The dosage will normally be administered once or several time per day.

The following Examples illustrate pharmaceutical compositions according to the present invention.

EXAMPLE 21

One thousand tablets for oral administration were prepared from the following compounds in manner known per se, each tablet containing 10 mg of the active substance.

| | |
|---|---|
| (E)-2-methyl-3-[4-(3-pyridylmethyl)phenyl]acrylic acid hydrochloride | 10 g |
| lactose | 30 g |
| Indian corn starch | 15 g |
| hydroxymethylcellulose | 30 g |
| calcium carboxymethylcellulose | 2 g |
| calcium stearate | 1 g |

By proceeding as described above, but replacing the (E)-2-methyl-3-[4-(3-pyridylmethyl)phenyl]acrylic acid hydrochloride by (E)-2-methyl-3-[4-(3-pyridylmethyl)phenyl]acrylic acid mesylate, (E)-2-methyl-3-[4-(3-pyridylmethyl)phenyl]acrylic acid sodium salt, (E)-2-methyl-3-[4-(3-pyridylmethyl)phenyl]acrylic acid, (Z)-

2-bromo-3-[4-(3-pyridylmethyl)phenyl]acrylic acid hydrochloride, (E)-2-ethyl-3-[4-(3-pyridylmethyl)phenyl]acrylic acid hydrochloride or (E)-2-methyl-3-[4-(4-methyl-3-pyridylmethyl)phenyl]acrylic acid hydrochloride, there were obtained one thousand tablets for oral administration, each tablet containing 10 mg of the active substance.

EXAMPLE 22

(E)-2-Methyl-3-[4-(3-pyridylmethyl)phenyl]acrylic acid hydrochloride (5 g) and chlorobutanol (10 g) were dissolved in sterile water to make a final volume of 1000 ml. One thousand ampoules for administration by injection were prepared from the above solution in manner known per se, each ampoule containing 5 mg of the active substance.

By proceeding as described above, but replacing the (E)-2-methyl-3-[4-(3-pyridylmethyl)phenyl]acrylic acid hydrochloride by (E)-2-methyl-3-[4-(3-pyridylmethyl)phenyl]acrylic acid mesylate, (E)-2-methyl-3-[4-(3-pyridylmethyl)phenyl]acrylic acid sodium salt, (E)-2-methyl-3- [4-(3-pyridylmethyl)phenyl]acrylic acid sodium salt, (E)-2-methyl-3-[4-(3-pyridylmethyl)phenyl]acrylic acid, (Z)-2-bromo-3-[4-(3-pyridylmethyl)-phenyl]acid hydrochloride, (E)-2-, ethyl-3-[4-(3-pyridylmethyl)-phenyl ]acid phenyl]acrylic acid hydrochloride or (E)-2-methyl-3-[4-(4-methyl-3-pyridylmethyl)phenyl]acrylic acid hydrochloride, there were obtained one thousand ampoules for administration by injection, each ampoule containing 5 mg of the active substance.

We claim:
1. A pyridine derivative of the general formula

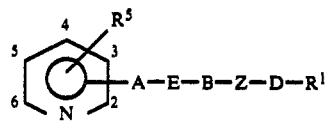

wherein A represents an alkylene group containing from 1 to 5 carbon atoms unsubstituted or substituted by a hydroxy group, B represents a single bond, or an alkylene group containing from 1 to 5 carbon atoms, D represents a single bond, or an alkylene group containing from 1 to 5 carbon atoms, E represents a grouping of the formula:

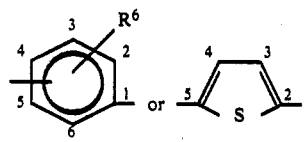

in which $R^6$ represents a hydrogen atom, or an alkyl group containing from 1 to 4 carbon atoms, Z represents a single bond, or an ethynylene group, or a grouping of the formula:

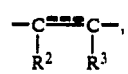

in which $R^2$ represents a hydrogen atom, or an alkyl group containing from 1 to 4 carbon atoms, $R^3$ represents a hydrogen, bromine or chlorine atom, or an alkyl group containing from 1 to 4 carbon atoms, the symbol ≡ represents a single or double bond, the carbon atom attached to $R^2$ binds to B, and the carbon atom attached to $R^3$ binds to D, $R^1$ represents a grouping of the formula: —COOR$^4$ or —COSR$^4$ in which $R^4$ represents a hydrogen atom, or an alkyl group containing from 1 to 12 carbon atoms, or an aralkyl group containing from 7 to 13 carbon atoms, or a cycloalkyl group containing from 4 to 7 carbon atoms unsubstituted or substituted by at least one alkyl group containing from 1 to 4 carbon atoms, or a phenyl group unsubstituted or substituted by at least one of a halogen atom, a trifluoromethyl group, an alkyl or alkoxy or alkylthio group, each containing from 1 to 4 carbon atoms, a nitro group or a phenyl group, $R^5$ represents a hydrogen atom, or an alkyl group containing from 1 to 4 carbon atoms, with the proviso that B, Z and D do not simultaneously each represent a single bond, and with the proviso that the pyridine ring is substituted by A at the 3- or 4-position thereof and non-toxic acid addition salts thereof and, when $R^1$ represents a carboxy or thiocarboxy group, non-toxic salts thereof.

2. A pyridine derivative according to claim 1 where A represents an alkylene group containing from 1 to 5 carbon atoms, B and D, which may be the same or different, each represent a single bond, or an alkylene group containing from 1 to 5 carbon atoms, Z represents a single bond, an ethynylene group, or a group

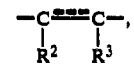

in which $R^2$, $R^3$ and the symbol ≡ are as defined in claim 1, $R^1$ represents a grouping of the formula —COOR$^4$, in which $R^4$ represents a hydrogen atom, or an alkyl group containing from 1 to 12 carbon atoms, $R^5$ represents a hydrogen atom, and E represents a grouping of the formula:

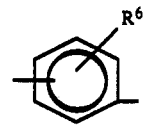

in which $R^6$ represents a hydrogen atom, and non-toxic acid addition salts thereof and when $R^1$ represents a carboxy group, non-toxic salts thereof.

3. A pyridine derivative according to claim 1 wherein A represents an alkylene group containing from 1 to 5 carbon atoms, $R^1$ represents a grouping of the formula: —COOR$^4$, in which $R^4$ represents a hydrogen atom, or an alkyl group containing from 1 to 12 carbon atoms, $R^5$ represents an alkyl group containing from 1 to 4 carbon atoms, and E represents a grouping of the formula:

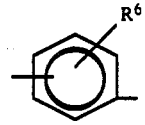

in which $R^6$ represents a hydrogen atom, and non-toxic acid addition salts thereof and when $R^1$ represents a carboxy group, non-toxic salts thereof.

4. A pyridine derivative according to claim 1 wherein A represents an alkylene group containing 1 or 2 carbon atoms unsubstituted or substituted by a hydroxy group.

5. A pyridine derivative according to claim 1 wherein B represents a single bond.

6. A pyridine derivative according to claim 1 wherein Z represents a single bond, or a group

7. A pyridine derivative according to claim 1 wherein E represents a group

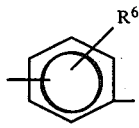

8. A pyridine derivative according to claim 1 wherein the benzene ring represented by E is substituted by A at the 4-position thereof and substituted by $R^6$ at the 3-position thereof, or vice versa.

9. A pyridine derivative according to claim 1 wherein the benzene ring represented by E is substituted by A at the 3- or 4-position thereof.

10. A pyridine derivative according to claim 1 wherein $R^1$ represents a group —COOR$^4$ or —COSR$^4$, in which $R^4$ represents a hydrogen atom, or an alkyl group containing from 1 to 10 carbon atoms, or an aralkyl group containing from 7 to 13 carbon atoms, or a phenyl group unsubstituted or substituted by at least one alkyl group containing from 1 to 4 carbon atoms, or a trifluoromethyl group.

11. A pyridine derivative according to claim 1 wherein $R^1$ represents a group —COOR$^4$ or —COSR$^4$, in which $R^4$ represents a hydrogen atom, or an alkyl group containing from 1 to 4 carbon atoms, or a decyl, benzyl, biphenylmethyl, 3-trifluoromethylphenyl, 3,5-di-tert-butylphenyl, 2-methylphenyl or phenyl group.

12. A pyridine derivative according to claim 1 wherein the pyridine ring is substituted by A at the 3-position thereof and substituted by $R^5$ at the 4-position thereof, or vice versa.

13. A pyridine derivative according to claim 1 which is (E)-3-[4-(3-pyridylmethyl)phenyl]acrylic acid methyl ester.

14. A pyridine derivative according to claim 1 which is (E)-3-[4-(3-pyridylmethyl)phenyl]acrylic acid ethyl ester.

15. A pyridine derivative according to claim 1 which is (E)-2-methyl-3-[4-(3-pyridylmethyl)phenyl]acrylic acid ethyl ester.

16. A pyridine derivative according to claim 1 which is (Z)-2-bromo-3-[4-(3-pyridylmethyl)phenyl]acrylic acid methyl ester.

17. A pyridine derivative according to claim 1 which is (E)-3-[4-(3-pyridylhydroxymethyl)phenyl]acrylic acid ethyl ester.

18. A pyridine derivative according to claim 1 which is (E)-2-methyl-3-[4-(1-3′-pyridylethyl)phenyl]acrylic acid ethyl ester.

19. A pyridine derivative according to claim 1 which is (E)-2-methyl-3-[4-(4-methyl-3-pyridylmethyl)phenyl]acrylic acid ethyl ester.

20. A pyridine derivative according to claim 1 which is (E)-2-methyl-3-[3-methyl-4-(3-pyridylhydroxymethyl)phenyl]acrylic acid ethyl ester.

21. A pyridine derivative according to claim 1 which is (E)-3-[3-methyl-4-(3-pyridylhydroxymethyl)phenyl]acrylic acid ethyl ester.

22. A pyridine derivative according to claim 1 which is (E)-2-methyl-3-[3-(3-pyridylhydroxymethyl)phenyl]acrylic acid ethyl ester.

23. A pyridine derivative according to claim 1 which is (E)-2-methyl-3-[3-(4-pyridylhydroxymethyl)phenyl]acrylic acid ethyl ester.

24. A pyridine derivative according to claim 1 which is (E)-5-(3-pyridylmethyl)-2-(2-ethoxycarbonylvinyl)-thiophene.

25. A pyridine derivative according to claim 1 which is (E)-5-(3-pyridylmethyl)-2-(2-ethoxycarbonyl-1-propenyl)thiophene.

26. A pyridine derivative according to claim 1 which is (E)-2-methyl-3-[4-(4-pyridylhydroxymethyl)phenyl]acrylic acid ethyl ester.

27. A pyridine derivative according to claim 1 which is (E)-3-[4-(1-3′-pyridylethyl)phenyl]acrylic acid ethyl ester.

28. A pyridine derivative according to claim 1 which is (E)-2-ethyl-3-[4-(3-pyridylmethyl)phenyl]acrylic acid ethyl ester.

29. A pyridine derivative according to claim 1 which is (E)-3-[4-(3-pyridylmethyl)phenyl]-2-butenoic acid ethyl ester.

30. A pyridine derivative according to claim 1 which is 2,2-dimethyl-3-[4-(3-pyridylmethyl)phenyl]propionic acid ethyl ester.

31. A pyridine derivative according to claim 1 which is (E)-2-methyl-3-[3-methyl-4-(3-pyridylmethyl)phenyl]acrylic acid ethyl ester.

32. A pyridine derivative according to claim 1 which is (E)-3-[3-methyl-4-(3-pyridylmethyl)phenyl]acrylic acid ethyl ester.

33. A pyridine derivative according to claim 1 which is (E)-2-methyl-3-[3-(3-pyridylmethyl)phenyl]acrylic acid ethyl ester.

34. A pyridine derivative according to claim 1 which is (E)-2-methyl-3-[3-(4-pyridylmethyl)phenyl]acrylic acid ethyl ester.

35. A pyridine derivative according to claim 1 which is (E)-2-methyl-3-[4-(4-pyridylmethyl)phenyl]acrylic acid ethyl ester.

36. A pyridine derivative according to claim 1 which is 3-[4-(3-pyridylmethyl)phenyl]propionic acid ethyl ester.

37. A pyridine derivative according to claim 1 which is 2-methyl-3-[4-(3-pyridylmethyl)phenyl]propionic acid ethyl ester.

38. A pyridine derivative according to claim 1 which is 3-[4-(3-pyridylhydroxymethyl)phenyl]propionic acid ethyl ester.

39. A pyridine derivative according to claim 1 which is 2-methyl-3-[4-(1-3′-pyridylethyl)phenyl]propionic acid ethyl ester.

40. A pyridine derivative according to claim 1 which is 3-[4-(1-3′-pyridylethyl)phenyl]propionic acid ethyl ester.

41. A pyridine derivative according to claim 1 which is 3-[4-(3-pyridylmethyl)phenyl]butyric acid ethyl ester.

42. A pyridine derivative according to claim 1 which is (E)-2-methyl-3-[4-(3-pyridylmethyl)phenyl]acrylic acid decyl ester.

43. A pyridine derivative according to claim 1 which is (E)-2-methyl-3-[4-(3-pyridylmethyl)phenyl]acrylic acid benzyl ester.

44. A pyridine derivative according to claim 1 which is (E)-2-methyl-3-[4-(3-pyridylmethyl)phenyl]acrylic acid biphenylmethyl ester.

45. A pyridine derivative according to claim 1 which is (E)-2-methyl-3-[4-(3-pyridylmethyl)phenyl]acrylic acid butyl ester.

46. A pyridine derivative according to claim 1 which is (E)-2-methyl-3-[4-(3-pyridylmethyl)phenyl]acrylic acid phenyl ester.

47. A pyridine derivative according to claim 1 which is (E)-2-methyl-3-[4-(3-pyridylmethyl)phenyl]acrylic acid 3-trifluoromethylphenyl ester.

48. A pyridine derivative according to claim 1 which is (E)-2-methyl-3-[4-(3-pyridylmethyl)phenyl]acrylic acid 3,5-di-tert-butylphenyl ester.

49. A pyridine derivative according to claim 1 which is (E)-2-methyl-3-[4-(3-pyridylmethyl)phenyl]acrylic acid 2-methylphenyl ester.

50. A pyridine derivative according to claim 1 which is (E)-2-methyl-3-[4-(3-pyridylmethyl)phenyl]thioacrylic S-acid S-ethyl ester.

51. A pyridine derivative according to claim 1 which is 4-(3-pyridylmethyl)phenylacetic acid.

52. A pyridine derivative according to claim 1 which is (E)-3-[4-(3-pyridylmethyl)phenyl]acrylic acid.

53. A pyridine derivative according to claim 1 which is 3-[4-(3-pyridylmethyl)phenyl]propionic acid.

54. A pyridine derivative according to claim 1 which is (E)-2-methyl-3-[4-(3-pyridylmethyl)phenyl]acrylic acid.

55. A pyridine derivative according to claim 1 which is 2-methyl-3-[4-(3-pyridylmethyl)phenyl]propionic acid.

56. A pyridine derivative according to claim 1 which is (Z)-2-bromo-3-[4-(3-pyridylmethyl)phenyl]acrylic acid.

57. A pyridine derivative according to claim 1 which is 2,2-dimethyl-3-[4-(3-pyridylmethyl)phenyl]propionic acid.

58. A pyridine derivative according to claim 1 which is (E)-2-ethyl-3-[4-(3-pyridylmethyl)phenyl]acrylic acid.

59. A pyridine derivative according to claim 1 which is (E)-3-[4-(3-pyridylhydroxymethyl)phenyl]acrylic acid.

60. A pyridine derivative according to claim 1 which is (E)-2-methyl-3-[4-(13'-pyridylethyl)phenyl]acrylic acid.

61. A pyridine derivative according to claim 1 which is (E)-2-methyl-3-[4-(4-methyl-3-pyridylmethyl)phenyl]acrylic acid.

62. A pyridine derivative according to claim 1 which is (E)-5-(3-pyridylmethyl)-2-(2-carboxyvinyl)thiophene.

63. A pyridine derivative according to claim 1 which is (E)-5-(3-pyridylmethyl)-2-(2-carboxy-1-propenyl)thiophene.

64. A pyridine derivative according to claim 1 which is (E)-3-[4(3-pyridylmethyl)phenyl]-2-butenoic acid.

65. A pyridine derivative according to claim 1 which is (E)-2-methyl-3-[3-methyl-4-(3-pyridylmethyl)phenyl]acrylic acid.

66. A pyridine derivative according to claim 1 which is (E)-3-[3-methyl-4-(3-pyridylmethyl)phenyl]acrylic acid.

67. A pyridine derivative according to claim 1 which is (E)-2-methyl-3-[3-(3-pyridylmethyl)phenyl]acrylic acid.

68. A pyridine derivative according to claim 1 which is (E)-2-methyl-3-[3-(4-pyridylmethyl)phenyl]acrylic acid.

69. A pyridine derivative according to claim 1 which is (E)-2-methyl-3-[4-(4-pyridylmethyl)phenyl]acrylic acid.

70. A pyridine derivative according to claim 1 which is 3-[4-(3-pyridylhydroxymethyl)phenyl]propionic acid.

71. A pyridine derivative according to claim 1 which is 2methyl-3-[4-(1-3'-pyridylethyl)phenyl]propionic acid.

72. a pyridine derivative according to claim 1 which is 3-[4-(1-3'-pyridylethyl)phenyl]propionic acid.

73. A pyridine derivative according to claim 1 which is 3-[4-(3-pyridylmethyl)phenyl]butyric acid.

74. A non-toxic salt of a pyridine derivative according to claim 1.

75. A non-toxic acid addition salt of a pyridine derivative according to claim 1.

76. A pharmaceutical composition which comprises, as an active ingredient, an effective amount of at least one pyridine derivative as claimed in claim 1 and a non-toxic acid addition salt thereof and, when $R^1$ represents a carboxy or thiocarboxy group, a non-toxic salt thereof, in association with a pharmaceutical carrier or coating.

* * * * *